(12) United States Patent
Wang et al.

(10) Patent No.: US 10,179,133 B2
(45) Date of Patent: *Jan. 15, 2019

(54) PYRROLOPYRIMIDINE COMPOUNDS FOR THE TREATMENT OF CANCER

(71) Applicant: The University of North Carolina at Chapel Hill, Chapel Hill, NC (US)

(72) Inventors: Xiaodong Wang, Chapel Hill, NC (US); Jing Liu, Jersey City, NJ (US); Weihe Zhang, Vestavia, AL (US); Stephen Frye, Chapel Hill, NC (US); Dmitri Kireev, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,700

(22) Filed: Oct. 23, 2017

(65) Prior Publication Data

US 2018/0104247 A1    Apr. 19, 2018

Related U.S. Application Data

(60) Continuation of application No. 15/014,573, filed on Feb. 3, 2016, now Pat. No. 9,795,606, which is a division of application No. 14/348,805, filed as application No. PCT/US2012/058298 on Oct. 1, 2012, now Pat. No. 9,273,056.

(60) Provisional application No. 61/542,392, filed on Oct. 3, 2011, provisional application No. 61/547,183, filed on Oct. 14, 2011.

(51) Int. Cl.
| | | |
|---|---|---|
| A61K 31/5377 | (2006.01) |
| A61K 31/519 | (2006.01) |
| C07D 487/04 | (2006.01) |
| C07D 487/18 | (2006.01) |

(52) U.S. Cl.
CPC ........ A61K 31/519 (2013.01); A61K 31/5377 (2013.01); C07D 487/04 (2013.01); C07D 487/18 (2013.01)

(58) Field of Classification Search
CPC ................ C07D 487/04; C07D 487/18; A61K 31/5377; A61K 31/519
See application file for complete search history.

(56) References Cited

U.S. PATENT DOCUMENTS

| | | | |
|---|---|---|---|
| 5,958,930 A | 9/1999 | Gangjee et al. |
| 7,589,086 B2 | 9/2009 | Bondavalli et al. |
| 7,897,607 B2 | 3/2011 | Gyorkos et al. |
| 7,956,060 B2 | 6/2011 | Arai et al. |
| 7,998,978 B2 | 8/2011 | Huang et al. |
| 8,324,225 B2 | 12/2012 | Brain et al. |
| 8,362,023 B2 | 1/2013 | Liu et al. |
| 8,415,361 B2 | 4/2013 | Lemke et al. |
| 8,513,242 B2 | 8/2013 | Chiang et al. |
| 9,290,499 B2 | 3/2016 | Wang et al. |
| 9,555,030 B2 | 1/2017 | Wang et al. |
| 9,555,031 B2 | 1/2017 | Wang et al. |
| 9,562,047 B2 | 2/2017 | Wang et al. |
| 9,567,326 B2 | 2/2017 | Wang et al. |
| 9,603,850 B2 | 3/2017 | Wang et al. |
| 9,649,309 B2 | 5/2017 | Wang et al. |
| 2004/0209895 A1 | 10/2004 | Luecking et al. |
| 2006/0025383 A1 | 2/2006 | Wishart et al. |
| 2007/0078140 A1 | 4/2007 | Borzilleri et al. |
| 2007/0105874 A1 | 5/2007 | Zhang et al. |
| 2007/0225306 A1 | 9/2007 | Choi et al. |
| 2007/0275984 A1 | 11/2007 | Irnogal et al. |
| 2008/0248046 A1 | 10/2008 | Ni et al. |
| 2008/0267887 A1 | 10/2008 | Yuan et al. |
| 2009/0012060 A1 | 1/2009 | Arai et al. |
| 2010/0137313 A1 | 6/2010 | Borjack-Sjodin et al. |
| 2010/0247554 A1 | 9/2010 | Lemke et al. |
| 2010/0266604 A1 | 10/2010 | Rothlin et al. |
| 2011/0281867 A1 | 11/2011 | Kalman et al. |
| 2011/0319267 A1 | 12/2011 | Ekwuribe et al. |
| 2012/0035194 A1 | 2/2012 | Huang et al. |
| 2012/0207763 A1 | 8/2012 | Brain et al. |
| 2012/0207764 A1 | 8/2012 | Terrett |

(Continued)

FOREIGN PATENT DOCUMENTS

| | | |
|---|---|---|
| EP | 1710246 A1 | 10/2006 |
| EP | 1803723 A1 | 7/2007 |

(Continued)

OTHER PUBLICATIONS

Aly et al. "Heteroannelations with o-amino aldehyde and o-amino cyanic of some pyrazole derivatives," Afinidad, Jan. 1, 2004; 61(514): 510-515.

Angelillo-Scherrer, A., et al., "Role of Gas6 receptors in platelet signaling during thrombus stabilization and implications for antithrombotic therapy," J. Clin. Invest. (2005) 115(2), 237-246.

Banker et al. Modern Pharmaceuticals p. 596 (1996).

Bernsmeier, et al., "Patients with Acute-on-Chronic Liver Failure Have Increased Numbers of Regulatory Immune Cells Expressing the Receptor Tyrosine Kinase MERTK" Gastroenterology (2015), 1-13.

(Continued)

*Primary Examiner* — Rebecca L Anderson
(74) *Attorney, Agent, or Firm* — Alston & Bird LLP

(57) ABSTRACT

Compounds of Formula I:

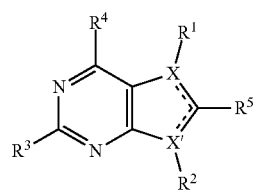

wherein: one of X and X' is N and the other of X and X' is C, are described, along with compositions containing the same and methods of use thereof in the treatment of cancer.

19 Claims, No Drawings

(56) References Cited

U.S. PATENT DOCUMENTS

| | | |
|---|---|---|
| 2012/0219559 A1 | 8/2012 | Chen et al. |
| 2012/0230991 A1 | 9/2012 | Graham et al. |
| 2013/0034862 A1 | 2/2013 | Fantl et al. |
| 2013/0059836 A1 | 3/2013 | Wang et al. |
| 2013/0072382 A1 | 3/2013 | Trullinger et al. |
| 2013/0102587 A1 | 4/2013 | Evans et al. |
| 2013/0137708 A1 | 5/2013 | Garske et al. |
| 2013/0150368 A1 | 6/2013 | Ashcratt et al. |
| 2013/0266563 A1 | 10/2013 | Gokaraju et al. |
| 2015/0291606 A1 | 10/2015 | Wang et al. |
| 2015/0291609 A1 | 10/2015 | Wang et al. |

FOREIGN PATENT DOCUMENTS

| | | | |
|---|---|---|---|
| WO | WO 1997/049706 A1 | 12/1997 | |
| WO | WO 2003/029209 A2 | 4/2003 | |
| WO | WO 2005/009443 A1 | 2/2005 | |
| WO | WO 2005/024434 A2 | 3/2005 | |
| WO | WO 2006/035067 A2 | 4/2006 | |
| WO | WO 2007/041379 A1 | 4/2007 | |
| WO | WO 2007/044426 A2 | 4/2007 | |
| WO | WO 2007/075554 A2 | 7/2007 | |
| WO | WO 2007/113254 A1 | 10/2007 | |
| WO | WO 2007/134828 A1 | 11/2007 | |
| WO | WO 2009/032694 A1 | 3/2009 | |
| WO | WO 2009/047359 A1 | 4/2009 | |
| WO | WO 2010/043865 A1 | 4/2010 | |
| WO | WO 2010/085597 A1 | 7/2010 | |
| WO | WO 2011/103441 A1 | 8/2010 | |
| WO | WO 2010/129802 A1 | 11/2010 | |
| WO | WO 2011/029915 A1 | 3/2011 | |
| WO | WO 2011/065800 A2 | 6/2011 | |
| WO | WO 2011/090760 A1 | 7/2011 | |
| WO | WO 2011/146313 A1 | 11/2011 | |
| WO | WO 2012/053606 A1 | 4/2012 | |
| WO | WO 2012/158795 A1 | 11/2012 | |
| WO | WO 2013/032591 A1 | 3/2013 | |
| WO | WO 2013/042006 A1 | 3/2013 | |
| WO | WO 2013/052417 A1 | 4/2013 | |
| WO | WO 2013/124324 A1 | 8/2013 | |
| WO | WO 2013/157022 A1 | 10/2013 | |
| WO | WO 2013/177168 A1 | 11/2013 | |
| WO | WO 2014/062774 A1 | 4/2014 | |
| WO | WO 2014/085225 A1 | 6/2014 | |
| WO | WO 2015/153978 | 10/2015 | |
| WO | WO 2015/157115 | 10/2015 | |
| WO | WO 2015/157122 | 10/2015 | |
| WO | WO 2015/157127 | 10/2015 | |
| WO | WO 2015/157128 | 10/2015 | |

OTHER PUBLICATIONS

Bhattacharayya, et al., "Enveloped viruses disable innate immune responses in dendritic cells by direct activation of TAM receptors," Cell Host & Microbe (2013) 14.

Brindley, et at, "Tyrosine kinase receptor Axl enhances entry of Zaire ebolavirus without direct interactions with the viral glycoprotein," Virology (2011) 415, 83-84.

Cavasotto et al. "In silico identification of novel EGFR inhibitors with antiproliferative activity against cancer cells," Bioorganic & Medicinal Chemistry Letters, 2006; 16: 1969-1974.

Chen, et al., "Identification of Gas6 as a ligand for Mer, a neural cell adhesion molecule related receptor tyrosine kinase implicated in cellular transformation," Oncogene (1997) 14, 2033-2039.

Chen, et al. "Mer Receptor tyrosine Kinase Signaling Participates in Platelet Function," Arterioscler. Thromb. Vasc. Biol. (2004) 24, 1118-1123.

Christoph, S. et al., "UNC569, a novel small-molecule Mer inhibitor with efficacy against acute lymphoblastic leukemia in vitro and in vivo" Mot. Cancer Ther (2013) 12(11):2367-77.

Cook., et al. "MerTK inhibition in tumor leukocytes decreases tumor growth and metastasis," J Clin Invest, 2013; 123: 3231-3242.

Database CAPLUS in STN, Ace. No. 2007:1144983, Guillemont et al., WO 2007/113254 A1 (Oct. 11, 2007) (abstract).

Earp, S. "Chemical Biology Consortium: Mer Kinase Inhibitor Studies" Presentation, Chemical Biology Consortium, Jan. 26, 2012.

European Search Report corresponding to European Application No. 13858929.6 dated May 3, 2016.

European Search Report corresponding to European Application No. 13847985.2 dated May 24, 2016.

Examination Report corresponding to European Application No. 13793925.2 dated Nov. 30, 2015.

Extended European Search Report, EP 11783985.2, dated Oct. 15, 2013.

Extended European Search Report, EP 12839069.7, dated May 4, 2015.

Frye, S. "Academic Drug Discovery and Chemical Biology" Presentation at the Northwestern 18th Annual Drug Discovery Symposium. Nov. 13, 2013.

Frye, S. "Academic Drug Discovery: US Perspective and Examples" Presentation, NCI Translational Science Meeting, Washington DC, Jul. 29, 2011.

Graham, et al., "Cloning and mRNA expression analysis of a novel human protooncogene, c-mer" Cell Growth Differ. (1994) 5, 647-657.

International Search Report and Written Opinion, PCT/US2011/036215, dated Aug. 16, 2011.

International Search Report and Written Opinion, PCT/US2012/058298, dated Dec. 12, 2012.

International Search Report and Written Opinion, PCT/US2013/042033, dated Aug. 27, 2013.

International Search Report and Written Opinion, PCT/US2015/24258, dated Jun. 24, 2015.

International Search Report and Written Opinion, PCT/US2015/24301, dated Jun. 25, 2015.

International Search Report and Written Opinion, PCT/US2015/24328, dated Jun. 25, 2015.

International Search Report and Written Opinion, PCT/US2015/24362, dated Jun. 26, 2015.

International Search Report and Written Opinion, PCT/US2015/24373, dated Jul. 7, 2015.

International Search Report and Written Opinion, PCT/US2015/24380, dated Jul. 1, 2015.

International Search Report and Written Opinion. PCT/US2015/24381, dated Jul. 1, 2015.

International Preliminary Report on Patentability, PCT/US2013/042033, dated Dec. 4, 2014.

Lee-Sherick, et al. "Efficacy of a Mer and Flt3 tyrosine kinase small molecule inhibitor, UNC1666, in acute myeloid leukemia," Oncotarget, Advance Publications, Feb. 10, 2015.

Linger, et al. "Mer receptor tyrosine kinase is a therapeutic target in pre-B-cell acute lyrnphoblastic leukemia" Blood, 2013; 122(9); 1599-1609.

Liu, J. et al. "Discovery of Novel Small Molecule Mer Kinase Inhibitors for the Treatment of Pediatric Acute Lymphoblastic Leukemia" ACS Med Chem Lett., Feb. 9, 2012; 3(2): 129-134.

Liu, J., et al., "UNC1062, a new and potent Mer inhibitor," Eur. J. Med. Chem. (2013) 65, 83-93.

Meertens, L., et al. "The TIM and TAM families of phosphatidylserine receptors mediate dengue virus entry" Cell Host & Microbe (2012) 12, 544-557.

Mercer, J., et al., "Vaccinia virus uses macropinocytosis and apoptotic mimicry to enter host cells," Science (2008) 320, 531-535.

Morizono, et al, "The Soluble Serum Protein Gas6 Bridges Virion Envelope Phosphatidylserine to the TAM Receptor Tyrosine Kinase Axl to mediate Viral Entry," Cell Host & Microbe (2011) 9, 286.298.

Morizono, et al., "Role of Phosphatidyl Receptors in Enveloped Virus Infection," J. Virology (2014) 88(8), 4275-4290.

Paolino, M., et al., "The E3 ligase Cbl-b and TAM receptors regulate cancer metastasis via natural killer cells," Nature (2014) 507:508-512.

(56) References Cited

OTHER PUBLICATIONS

Powell et al., "Highly selective 2,4-diaminopyridine-5-carboxamide inhibitors of Sky kinase," Bioorg. Med. Chem. Lett. (2013) 23, 1046-1050.
Powell et al., "Optimization of highly selective 2,4-diaminopyridine-5-carboxamide inhibitors of Sky kinase," Bioorg. Med. Chem. Lett. (2013) 23, 1051-1055.
Sather, et al., "A soluble form of the Mer receptor tyrosine kinase inhibits macrophage clearance of apoptotic cells and platelet aggregation," Blood (2007) 109(3), 1026-1033.
Schlegel et al., "MER receptor tyrosine kinase is a therapeutic target in melanoma" J Clin Invest, May 2013; 123(5); 2257-67.
Shimojima, et al., "Tyro3 Family-mediated Cell Entry of Ebola and Marburg Viruses" Journal of Virology (2006) 80(20), 10109-10116.
Wolff et al., "Burger's Medicinal Chemistry and Drug Discovery", John Wiley & Sons, Inc. 5th Ed. vol. 1:975-977 (1995).
Zhang, W., et al., "Discovery of Mer specific tyrosine kinase inhibitors for the treatment and prevention of thrombosis," J. Med. Chem. (2013) 56, 9693-9700.
Zhang, W., et al., "Pseudo-cyclization through intramolecular hydrogen bond enables discovery of pyridine substituted pyrimidines as new Mer kinase inhibitors," J. Med. Chem. (2013) 56, 9683-9692.
Unpublished International Application No. PCT/US15/024393 filed on Apr. 4, 2015 by the University of North Carolina at Chapel Hill.
Unpublished International Application No. PCT/US15/024395 filed on Apr. 3, 2015 by the University of North Carolina at Chapel Hill.
Unpublished International Application No. PCT/US15/024396 filed on Apr. 4, 2015 by the University of North Carolina at Chapel Hill.

PYRROLOPYRIMIDINE COMPOUNDS FOR THE TREATMENT OF CANCER

RELATED APPLICATIONS

This application is a continuation of U.S. patent application Ser. No. 15/014,573, filed Feb. 3, 2016, which is a divisional of U.S. patent application Ser. No. 14/348,805, filed Mar. 31, 2014, and subsequently issued as U.S. Pat. No. 9,273,056 on Mar. 1, 2016, which is a 35 U.S.C. § 371 national phase entry of International Application No. PCT/US2012/058298, filed Oct. 1, 2012, and published in English on Apr 11, 2013, as International Publication No. WO 2013/052417, and which claims the benefit of U.S. Provisional Applications Ser. Nos. 61/542,392, filed Oct. 3, 2011, and 61/547,183, filed Oct. 14, 2011, the disclosures of each of which are incorporated by reference herein in their entirety.

This application is related to PCT Application No. PCT/US2011/036215 filed May 12, 2011.

STATEMENT OF FEDERAL SUPPORT

This invention was made with government support under Grant No. HHSN261200800001E awarded by the National Institutes of Health. The Government has certain rights in the invention.

FIELD OF THE INVENTION

The present invention concerns compounds, compositions and methods for the treatment of cancer.

BACKGROUND OF THE INVENTION

Acute Lymphoblastic Leukemia (ALL) is the most common malignancy in children and common varieties are cured by chemotherapy in 75%-85% of the cases. Collectively the less common T cell and rare B cell subsets represent less than 2000 cases yearly and thus can be classified as a rare disease; these subsets have a poorer prognosis. Unfortunately with either subset, resistance to and relapse from therapy is a major cause of pediatric cancer death. In addition, ALL chemotherapies can cause late complications that are increasingly recognized in pediatric survivor populations. In fact, in pediatric cancer survivors, the incidence of severe late effects (neurocognitive sequelae, auditory complications, cardiovascular dysfunction, gastrointestinal/hepatic dysfunction, growth delay, secondary malignancies, and infertility) directly related to therapy is approximately 25%. A better understanding of therapeutic resistance and its reversal could not only help those who relapse but may help lower the dose of chemotherapy needed in ALL patients thus reducing long-term toxicity for future survivors.

SUMMARY OF THE INVENTION

The ectopic expression of Mer receptor tyrosine kinase (Mer) has been identified as a tumor cell survival gene product in Acute Lymphoblastic Leukemia (ALL) cells and a potential cause of ALL chemoresistance. Hence, we investigated whether the development of small molecule Mer inhibitors was possible.

A first aspect of the present invention is a compound (sometimes referred to as an "active compound" herein) of Formula I, IA, or IB:

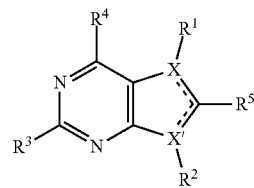

(I)

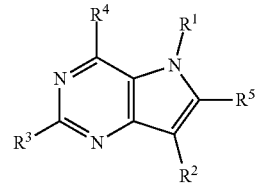

(IA)

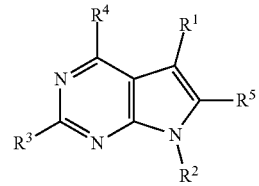

(IB)

wherein:
one of X and X' is N and the other of X and X' is C;
one of the dashed lines in Formula I is a single bond and the other of the dashed lines is a double bond (e.g., as shown in Formulas IA and IB);
$R^1$ is aryl;
$R^2$ is —$R^5R^6$, where $R^5$ is a covalent bond or C1 to C3 alkyl and $R^6$ is cycloalkyl, heterocycloalkyl, aryl, heteroaryl or alkyl, and wherein $R^6$ is optionally substituted from one to two times with independently selected polar groups;
$R^3$ is —$NR^7R^8$, where $R^7$ and $R^8$ are each independently selected from H, alkyl, arylalkyl; cycloalkylalkyl, heterocycloalkylalkyl, heteroaryalkyl, and alkoxyalkyl, each of which is optionally substituted one, two or three times with independently selected polar groups;
or $R^2$ and $R^3$ together form a linking group;
$R^4$ is H, loweralkyl, halo, or loweralkoxy;
$R^5$ is H, loweralkyl, halo, or loweralkoxy;
or a pharmaceutically acceptable salt or prodrug thereof.

A further aspect of the invention is an active compound as desecribed herein in a pharmaceutically acceptable interior.

A further aspect of the invention is a method of treating cancer in a subject in need thereof, comprising administering said subject an active compound as described herein in an amount effective to treat the cancer.

A further aspect of the invention is an active compound as described herein for use in treating cancer, and/or for the preparation of a medicament for the treatment of cancer.

DETAILED DESCRIPTION OF PREFERRED EMBODIMENTS

"Deuterium" as used herein alone or as part of another group, refers to a safe, non-radioactive relative of hydrogen. Any hydrogen may be replaced with deuterium to modify/improve metabolic stability, resulting in better safety, tolerability and/or efficacy.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms.

Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2- butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise. "Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical—NHR, where R is an alkyl group.

"Arylalkylamino" as used herein alone or as part of another group means the radical—NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical—$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl. "Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Linking group" as used herein are generally bivalent aromatic, aliphatic, or mixed aromatic and aliphatic groups. Thus linking groups include linear or branched, substituted or unsubstituted aryl, alkyl, alkylaryl, or alkylarylalkyl linking groups, where the alkyl groups are saturated or unsaturated, and where the alkyl and aryl groups optionally containing independently selected heteroatoms such as 1, 2, 3 or 4 heteroatoms selected from the group consisting of N, O, and S. In some embodiments, linking groups containing from 2 to 20 carbon atoms are preferred. Numerous examples of suitable linking groups are known, including but not limited to those described in, U.S. Pat. Nos. 8,247,572; 8,097,609; 6,624,317; 6,613,345; 6,596,935; and 6,420,377, the disclosures of which are incorporated by reference herein in their entirety.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of cancer. The other compounds may optionally be administered concurrently. As used herein, the word "concurrently" means sufficiently close in time to produce a combined effect (that is, concurrently may be simultaneously, or it may be two or more events occurring within a short time period before or after each other).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

1. Active compounds.

As noted above, the present invention provides active compounds of Formula I, IA, or IB:

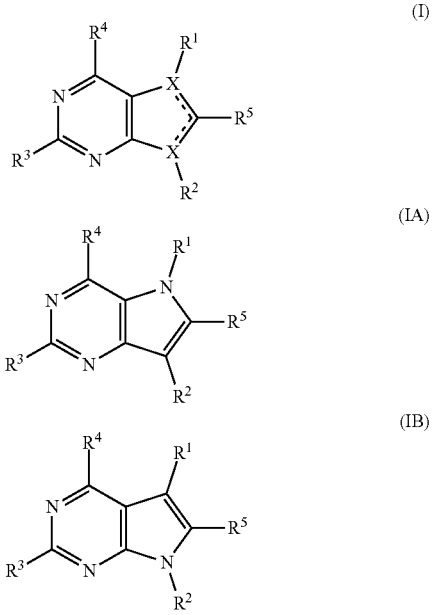

wherein:
one of X and X' is N and the other of X and X' is C;
one of the dashed lines is a single bond (between a ring carbon atom and a ring nitrogen atom) and the other of the dashed lines is a double bond (between two ring carbon atoms);
$R^1$ is aryl;
$R^2$ is —$R^5R^6$, where $R^5$ is a covalent bond or C1 to C3 alkyl and $R^6$ is cycloalkyl, heterocycloalkyl, aryl, heteroaryl or alkyl, and wherein $R^6$ is optionally substituted from one to two times with independently selected polar groups;
$R^3$ is —$NR^7R^8$, where $R^7$ and $R^8$ are each independently selected from H, alkyl, arylalkyl; cycloalkylalkyl, heterocycloalkylalkyl, heteroaryalkyl, and alkoxyalkyl, each of which is optionally substituted one, two or three times with independently selected polar groups; and
$R^4$ is H, loweralkyl, halo, or loweralkoxy;
or a pharmaceutically acceptable salt or prodrug thereof.
In some embodiments of the foregoing, $R^1$ is phenyl or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

In some embodiments of the foregoing $R^5$ is —$CH_2$—.
In some embodiments of the foregoing, $R^8$ is C1-C8 alkyl, C3-C8 cycloalkyl, or C1-C8 alkyl aryl.
In some embodiments of the foregoing, $R^6$ is cyclohexyl.
In some embodiments of the foregoing, $R^6$ is substituted once with amino.
In some embodiments of the foregoing, $R^7$ is H.
In some embodiments of the foregoing, $R^8$ is loweralkyl.
In some embodiments of the foregoing, $R^4$ is H.

Particular examples of compounds of the present invention include but are not limited to those set forth in Table 1 and Example 2 below.

Active compounds may be provided as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A. C. S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

2. Pharmaceutical formulations.

The active compounds described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2 M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and routes of administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. In some embodiments, a dosage from about 0.5 mg/kg to 5 mg/kg may be employed for intramuscular injection. In some embodiments, dosages are 1 µmol/kg to 50 µmol/kg, and more preferably 22 µmol/kg and 33 µmol/kg of the compound for intravenous or oral administration. The duration of the treatment can be once per day for a period of two to three weeks or until the condition is essentially controlled.

As noted above, the active compounds described herein are useful for the treatment of cancer. Example cancers that may be treated by the compounds and methods of the invention include, but are not limited to, myeloid leukemia, lymphoblastic leukemia, melanoma, breast, lung, colon, liver, gastric, kidney, ovarian, uterine, and brain cancer.

The present invention is explained in greater detail in the following non-limiting Examples.

Example 1

7-((Trans-4-aminocyclohexyl)methyl)-N-butyl-5-(4-fluorophenyl)-7H-pyrrolo[2,3-d]pyrimidin-2-amine General Procedure A:

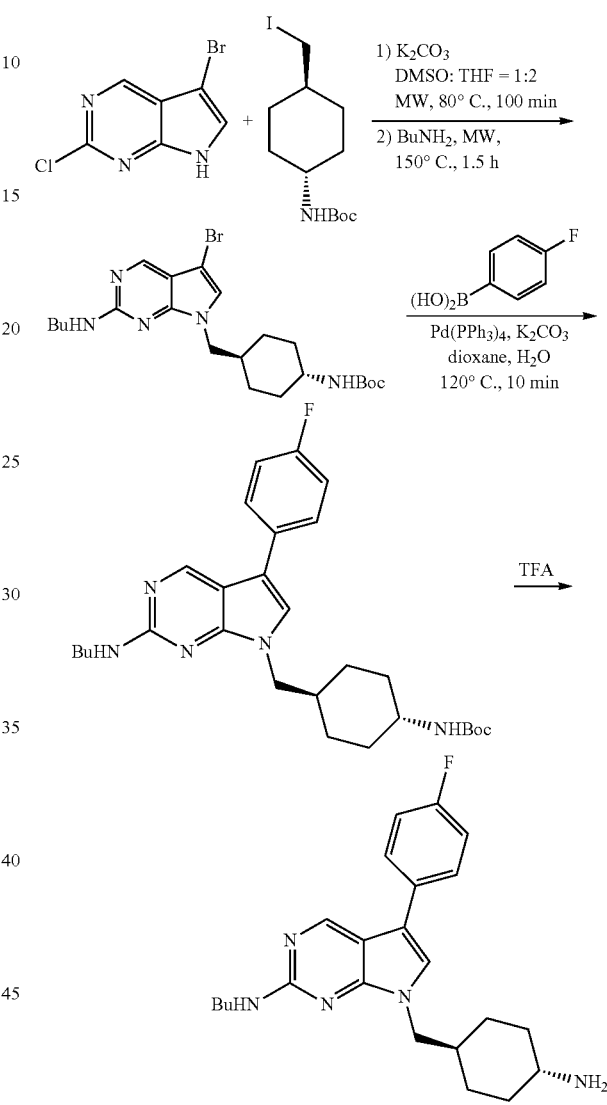

tert-Butyl trans-4-((5-bromo-2-(butylamino)-7H-pyrrolo[2,3-d]pyrimidin-7-yl)methyl)cyclohexylcarbamate

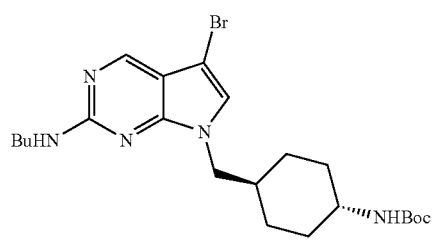

A 10 mL microwave tube was charged with 5-bromo-2-chloro-7H-pyrrolo[2,3-d]pyrimidine (0.23 g, 1.0 mmol), tert-butyl trans-4-(iodomethyl)cyclohexylcarbamate (0.51 g, 1.5 mmol), K₂CO₃ (0.28 g, 2.0 mmol), DMSO (1.5 mL) and THF (3 mL). The mixture was heated at 150° C. for 100 min in microwave. After the reaction mixture was cooled to ambient temperature, n-butylamine (0.18 g, 2.5 mmol) was added. The mixture was heated at 150° C. for 90 min in microwave. After cooling to ambient temperature, the reaction was poured into water and extracted with EtOAc (3X). The combined organic layer was dried (Na₂SO₄) and concentrated. The crude mixture was purified by Isco to provide tert-butyl trans-4-((5-bromo-2-(butylamino)-7H-pyrrolo[2,3-d]pyrimidin-7-yl)methyl)cyclohexylcarbamate (0.35 g, 73%) as a white solid. MS m/z 480.2 [M+H]⁺.

7-((Trans-4-aminocyclohexyl)methyl)-N-butyl-5-(4-fluorophenyl)-7H-pyrrolo[2,3-d]pyrimidin-2-amine

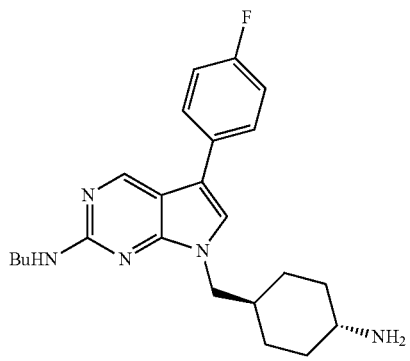

A 10 mL microwave tube was charged with tert-butyl trans-4-4-((5-bromo-2-(butylamino)-7H-pyrrolo[2,3-d]pyrimidin-7-yl)methyl)cyclohexylcarbamate (0.096 g, 0.20 mmol), 4-fluorophenylboronic acid (0.042 g, 0.30 mmol), potassium carbonate (0.055 g, 0.40 mmol), tetrakis(triphenylphosphine)palladium (0.024 g, 0.020 mmol), dioxane (2 mL) and water (0.50 mL). The reaction was heat at 120° C. for 10 min in microwave. The reaction was diluted with EtOAc and washed with water. The aqueous layer was extracted with EtOAc (3X). The combined organic layers were dried (Na₂SO₄), concentrated, and purified by Isco to provide tert-butyl trans-4-((2-(butylamino)-5-(4-fluorophenyl)-7H-pyrrolo[2,3-d]pyrimidin-7-yl)methyl)cyclohexylcarbamate. This intermediate was dissolved in CH₂Cl₂ (2 mL). Trifluoroacetic acid (0.6 mL) was added at ambient temperature. After stirring for 2 h, the solvent was evaporated. The residue was purified by preparative HPLC to provide 7-((trans-4-aminocyclohexyl)methyl)-N-butyl-5-(4-fluorophenyl)-7H-pyrrolo[2,3-d]pyrimidin-2-amine (UNC1537A) as a yellow solid (TFA salt) (UNC1537A) (0.032 g, 41%). ¹H NMR (400 MHz, CD₃OD) δ 8.76 (s, 1H), 7.67 (s, 1H), 7.67-7.61 (m, 2H), 7.21 (t, J=8.5 Hz, 2H), 4.10 (d, J =7.0 Hz, 2H), 3.54 (t, J =7.1 Hz, 2H), 3.16-3.01 (m, 1H), 2.07 (d, J =10.3 Hz, 2H), 2.04-1.92 (m, 1H), 1.85 (d, J =12.2 Hz, 2H), 1.76-1.65 (m, 2H), 1.54-1.44 (m, 2H), 1.44-1.34 (m, 2H), 1.34-1.20 (m, 2H), 1.01 (t, J=7.4 Hz, 3H); MS m/z 396.3 [M+H]⁺.

TABLE 1 describes compounds prepared following procedures described in Example 1 (General Procedure A), using appropriate reagents. (Note: Mer IC50: ++++ means <10 nM; +++ means between 10-100 nM, ++ means between 100 nM-1 μM; + means between 1-30 μM; – means inactive.)

| | Structure | Compound_ID | Mer IC$_{50}$ | Physical Data MS m/z (M + 1) or/and ¹H NMR (400 MHz, CD₃OD) |
|---|---|---|---|---|
| 1 | (structure shown) | UNC1532A | ++++ | ¹H NMR (400 MHz, CD₃OD) δ 8.73 (s, 1H), 7.59 (s, 1H), 7.56 (d, J = 8.7 Hz, 2H), 7.16-7.07 (m, 2H), 4.09 (d, J = 7.0 Hz, 2H), 3.92-3.83 (m, 4H), 3.54 (t, J = 7.1 Hz, 2H), 3.28-3.21 (m, 4H), 3.14-3.02 (m, 1H), 2.07 (d, J = 10.0 Hz, 2H), 2.03-1.92 (m, 1H), 1.84 (d, J = 11.9 Hz, 2H), 1.75-1.65 (m, 2H), 1.55-1.44 (m, 2H), 1.44-1.34 (m, 2H), 1.34-1.21 (m, 2H), 1.01 (t, J = 7.4 Hz, 3H); MS m/z 463.3 [M + H]⁺. |

TABLE 1-continued describes compounds prepared following procedures described in Example 1 (General Procedure A), using appropriate reagents. (Note: Mer IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 2 | 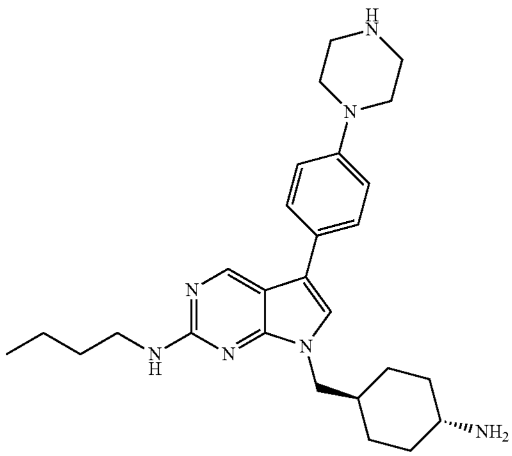 [SMILES: CCCCNc1ncc2c(-c3ccc(N4CCNCC4)cc3)cn(C[C@H]3CC[C@H](N)CC3)c2n1] | UNC1533A | ++++ | $^1$H NMR (400 MHz, CD$_3$OD) δ 8.74 (s, 1H), 7.60 (s, 1H), 7.58 (d, J = 8.8 Hz, 2H), 7.13 (d, J = 8.8 Hz, 2H), 4.09 (d, J = 7.0 Hz, 2H), 3.54 (t, J = 7.1 Hz, 2H), 3.51-3.44 (m, 4H), 3.43-3.37 (m, 4H), 3.13-3.02 (m, 1H), 2.07 (d, J = 9.9 Hz, 2H), 2.03-1.94 (m, 1H), 1.84 (d, J = 12.3 Hz, 2H), 1.76-1.65 (m, 2H), 1.54-1.44 (m, 2H), 1.44-1.34 (m, 2H), 1.34-1.20 (m, 2H), 1.01 (t, J = 7.4 Hz, 3H); MS m/z 462.3 [M + 1]$^+$. |
| 3 | 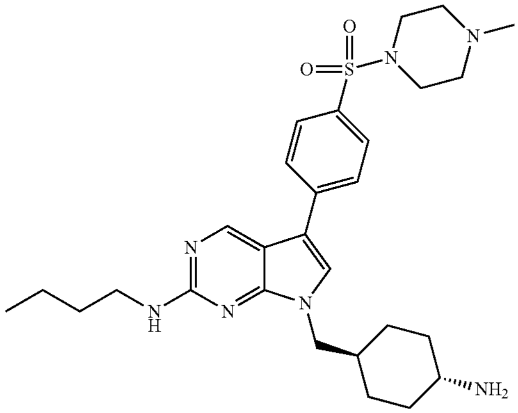 [SMILES: CCCCNc1ncc2c(-c3ccc(S(=O)(=O)N4CCN(C)CC4)cc3)cn(C[C@H]3CC[C@H](N)CC3)c2n1] | UNC1534A | ++++ | $^1$H NMR (400 MHz, CD$_3$OD) δ 8.90 (s, 1H), 7.98-7.85 (m, 5H), 4.14 (d, J = 7.0 Hz, 2H), 4.08-3.72 (bs, 2H), 3.69-3.42 (bs, 2H), 3.56 (t, J = 7.1 Hz, 2H), 3.31-3.15 (bs, 2H), 3.15-3.01 (m, 1H), 2.90 (s, 3H), 2.89-2.59 (bs, 2H), 2.08 (d, J = 10.0 Hz, 2H), 2.04-1.94 (m, 1H), 1.85 (d, J = 12.0 Hz, 2H), 1.77-1.66 (m, 2H), 1.55-1.45 (m, 2H), 1.45-1.35 (m, 2H), 1.35-1.21 (m, 2H), 1.02 (t, J = 7.4 Hz, 3H); MS m/z 540.3 [M + 1]$^+$. |

TABLE 1-continued

*describes compounds prepared following procedures described in Example 1 (General Procedure A), using appropriate reagents. (Note: Mer IC50: ++++ means <10 nM; +++ means between 10-100 nM, ++ means between 100 nM-1 µM; + means between 1-30 µM; − means inactive.)*

| | Structure | Compound_ID | Mer IC$_{50}$ | Physical Data MS m/z (M + 1) or/and $^1$H NMR (400 MHz, CD$_3$OD) |
|---|---|---|---|---|
| 4 | 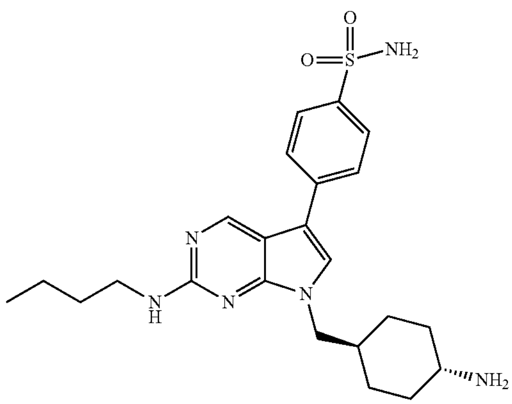 [SMILES: CCCCNc1ncc2c(-c3ccc(S(N)(=O)=O)cc3)cn(C[C@H]3CC[C@H](N)CC3)c2n1] | UNC1535A | ++++ | $^1$H NMR (400 MHz, CD$_3$OD) δ 8.86 (s, 1H), 7.98 (d, J = 8.5 Hz, 2H), 7.86 (s, 1H), 7.83 (d, J = 8.5 Hz, 2H), 4.12 (d, J = 7.0 Hz, 2H), 3.54 (t, J = 7.1 Hz, 2H), 3.16-3.01 (m, 1H), 2.08 (d, J = 10.3 Hz, 2H), 2.04-1.93 (m, 1H), 1.85 (d, J = 12.0 Hz, 2H), 1.77-1.65 (m, 2H), 1.55-1.44 (m, 2H), 1.43-1.34 (m, 2H), 1.34-1.20 (m, 2H), 1.01 (t, J = 7.4 Hz, 3H); MS m/z 457.3 [M + 1]$^+$. |
| 5 | 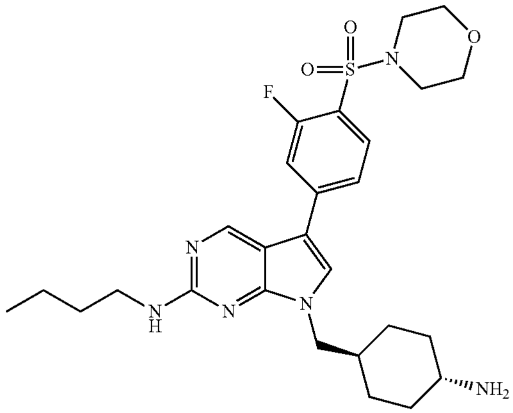 [SMILES: CCCCNc1ncc2c(-c3ccc(S(=O)(=O)N4CCOCC4)c(F)c3)cn(C[C@H]3CC[C@H](N)CC3)c2n1] | UNC1536A | ++++ | $^1$H NMR (400 MHz, CD$_3$OD) δ 8.92 (s, 1H), 7.98 (s, 1H), 7.83 (t, J = 7.9 Hz, 1H), 7.68-7.65 (m, 1H), 7.64 (s, 1H), 4.12 (d, J = 7.0 Hz, 2H), 3.76-3.65 (m, 4H), 3.55 (t, J = 7.1 Hz, 2H), 3.20-3.11 (m, 4H), 3.11-3.02 (m, 1H), 2.07 (d, J = 10.5 Hz, 2H), 2.04-1.94 (m, 1H), 1.86 (d, J = 11.9 Hz, 2H), 1.76-1.65 (m, 2H), 1.55-1.44 (m, 2H), 1.44-1.35 (m, 2H), 1.34-1.21 (m, 2H), 1.01 (t, J = 7.4 Hz, 3H); MS m/z 545.3 [M + 1]$^+$. |

Example 2

Trans-4-(2-(Butylamino)-5-(4-fluorophenyl) -7H-pyrrolo [2,3-d]pyrimidin-7-yl) cyclohexanol General Procedure B:

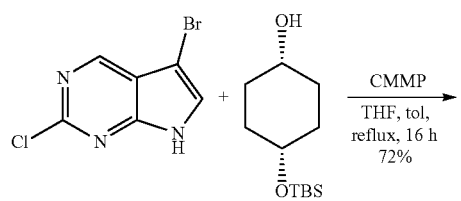

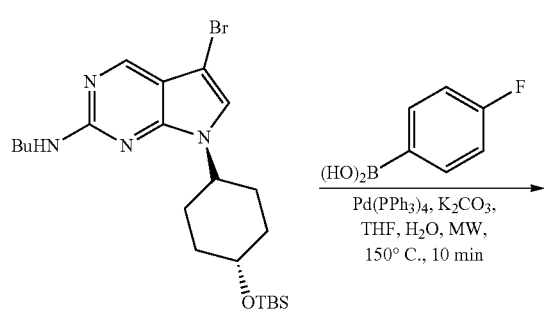

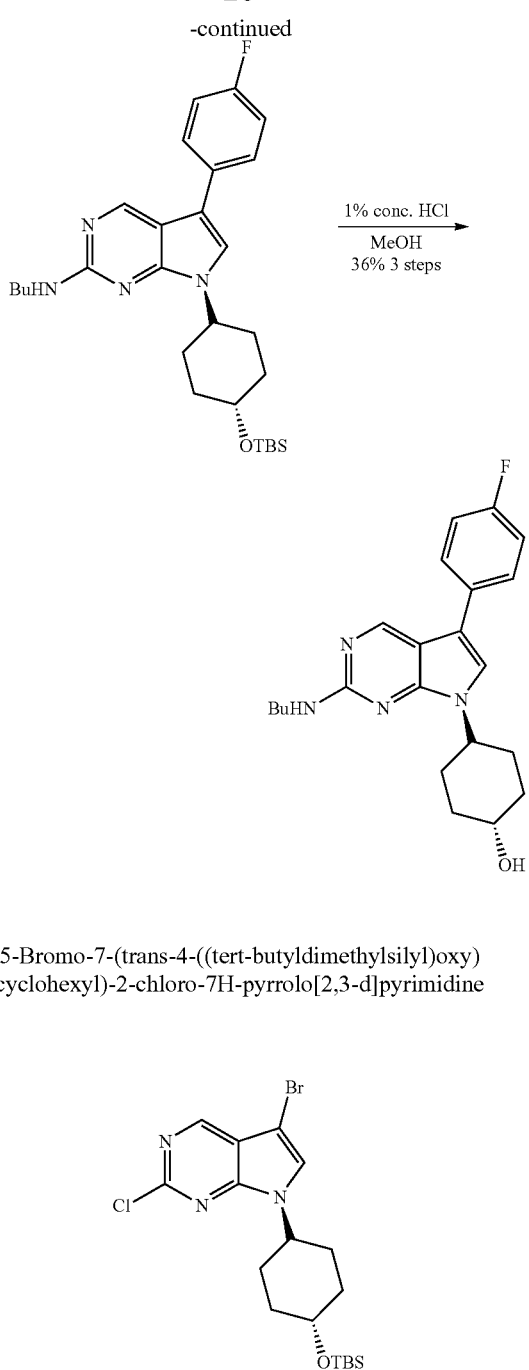

5-Bromo-7-(trans-4-((tert-butyldimethylsilyl)oxy) cyclohexyl)-2-chloro-7H-pyrrolo[2,3-d]pyrimidine To a suspension of 5-bromo-2-chloro-7H-pyrrolo[2,3-d] pyrimidine (0.13 g, 0.50 mmol) and cis-4-(tert-butyldimethylsilyloxy)cyclohexanol (0.23 g, 1.0 mmol) in toluene (8 mL) was added (cyanomethylene)trimethylphosphorane (CMMP; prepared according to Chem. Pharm. Bull. 2003, 51(4), 474-476.) (6.3 mL, 0.16 M in THF, 1.0 mmol). The resulting clear solution was refluxed for 16 h. The reaction mixture was washed with brine, and extracted with EtOAc (3X). The combined organic layer was dried ($Na_2SO_4$) and concentrated. The residue was purified on ISCO to provide the desired product (0.16 g, 72%). 1H NMR (400 MHz, $CD_3OD$) δ 8.71 (s, 1H), 7.27 (s, 1H), 4.70 (tt, J =12.2, 3.9 Hz, 1H), 3.69 (tt, J =10.5, 4.2 Hz, 1H), 2.09-1.99 (m, 3H), 1.86-1.71 (m, 2H), 1.66-1.54 (m, 3H), 0.90 (s, 9H), 0.08 (s, 6H). MS m/z 444.2 $[M+H]^+$.

Trans-4-(2-(butylamino)-5-(4-fluorophenyl)-7H-pyrrolo[2,3-d]pyrimidin-7-yl-cyclohexanol

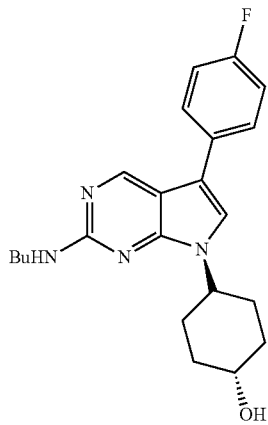

To a solution of 5-bromo-7-(trans-4-(tert-butyldimethylsilyloxy)cyclohexyl)-2-chloro-7H-pyrrolo[2,3-d]pyrimidine (0.082 g, 0.18 mmol) in isopropyl alcohol (2.0 mL) was added n-butylamine (0.033 g, 0.45 mmol) in a microwave tube. The resulting mixture was heated under microwave irradiation at 150° C. for 1.5 h. After the reaction cooled to room temperature, the solvent and excess amine was evaporated under vacuum. The residue was dissolved in THF and concentrated under vacuum (3X). Then it was dissolved in THF (2.0 mL) in a microwave tube. To this solution was added $K_2CO_3$ (0.050 g, 0.36 mmol), $Pd(PPh_3)_4$ (0.021 g, 0.018 mmol), (4-fluorophenyl)boronic acid (0.038 g, 0.27 mmol), and $H_2O$ (0.5 mL). The resulting mixture was heated under microwave irradiation at 150° C. for 10 min. After cooled to room temperature, it was washed with brine and extracted with EtOAc (5X). The combined organic layer was dried ($Na_2SO_4$) and concentrated. The residue was filtered through a short column of silica gel to provide N-butyl-7-(trans-4-((tert-butyldimethylsilyl)oxy) cyclohexyl)-5-(4-fluorophenyl)-7H-pyrrolo [2,3 -d]pyrimidin-2-amine which was used for next step without further purification.

A solution of crude N-butyl-7-(trans-4-((tert-butyldimethylsilyl)oxy) cyclohexyl)-5-(4-fluorophenyl)-7H-pyrrolo[2, 3-d]pyrimidin-2-amine in MeOH (2.0 mL) was added a concentrated HCl solution (3 drops, 37% in water). The resulting solution was stirred at room temperature overnight, then concentrated. The residue was purified by pre-HPLC to provide the desired product (UNC1671A) (0.025 g, 36% over 3 steps). 1H NMR (400 MHz, $CD_3OD$) δ 8.73 (s, 1H), 7.80 (s, 1H), 7.69-7.62 (m, 2H), 7.24-7.16 (m, 2H), 4.64-4.52 (m, 1H), 3.79-3.67 (m, 1H), 3.55 (t, J=7.1 Hz, 2H), 2.18-2.11 (m, 2H), 2.11-2.01 (m, 4H), 1.77-1.66 (m, 2H), 1.59-1.44 (m, 4H), 1.03 (t, J=7.4 Hz, 3H); MS m/z 383.2 $[M+H]^+$.

TABLE 2 describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 1 | 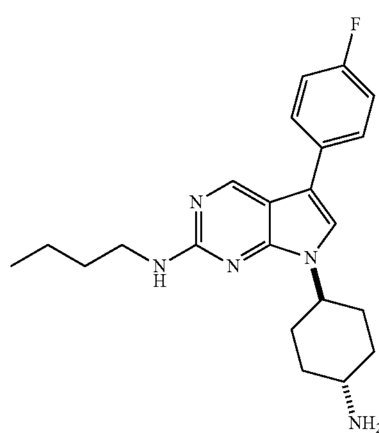 | UNC1970A | ++++ | $^1$H NMR (400 MHz, CD$_3$OD) δ 8.75 (s, 1H), 7.81 (s, 1H), 7.71-7.62 (m, 2H), 7.25-7.16 (m, 2H), 4.72-4.60 (m, 1H), 3.55 (t, J = 7.1 Hz, 2H), 2.30-2.22 (m, 2H), 2.23-2.03 (m, 4H), 1.79-1.63 (m, 4H), 1.55-1.44 (m, 2H), 1.02 (t, J = 7.4 Hz, 3H); MS m/z 382.25 [M + H]$^+$. |

TABLE 2-continued

*describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; – means inactive.)*

| | Structure | Compound_ID | Mer IC$_{50}$ | Physical Data MS m/z (M + 1) or/and $^1$H NMR (400 MHz, CD$_3$OD) |
|---|---|---|---|---|
| 2 | 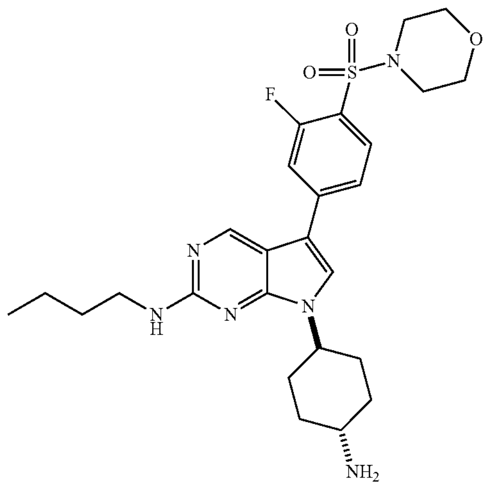 | UNC1971A | ++++ | $^1$H NMR (400 MHz, CD$_3$OD) δ 8.92 (s, 1H), 8.13 (s, 1H), 7.94-7.84 (m, 1H), 7.78-7.64 (m, 2H), 4.66 (dq, J = 9.8, 4.6 Hz, 1H), 3.75-3.68 (m, 4H), 3.56 (t, J = 7.1 Hz, 2H), 3.35-3.26 (m, 1H), 3.19-3.12 (m, 4H), 2.31-2.10 (m, 6H), 1.84-1.60 (m, 4H), 1.57-1.40 (m, 2H), 1.02 (t, J = 7.4 Hz, 3H); MS m/z 531.30 [M + H]$^+$. |
| 3 | 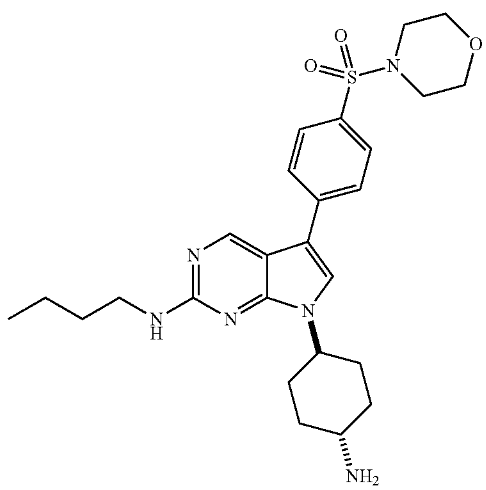 | UNC1972A | ++++ | $^1$H NMR (400 MHz, CD$_3$OD) δ 8.89 (s, 1H), 8.07 (s, 1H), 7.97-7.89 (m, 2H), 7.85 (d, J = 8.5 Hz, 2H), 4.73-4.64 (m, 1H), 3.74-3.70 (m, 4H), 3.56 (t, J = 7.1 Hz, 2H), 3.35-3.26 (m, 1H), 3.03-2.97 (m, 4H), 2.36-2.08 (m, 6H), 1.81-1.64 (m, 4H), 1.57-1.41 (m, 2H), 1.03 (t, J = 7.4 Hz, 3H); MS m/z 513.30 [M + H]$^+$. |
| 4 | 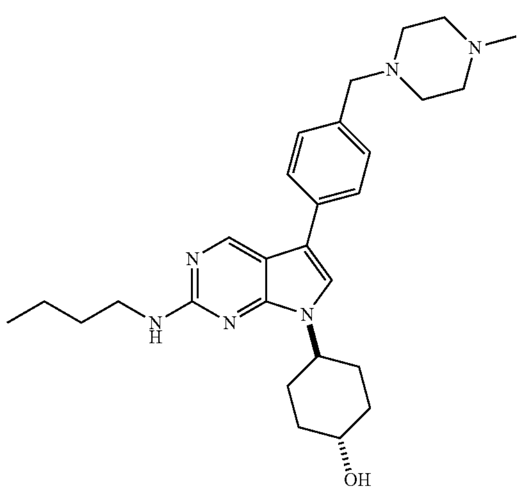 | UNC2025A | ++++ | $^1$H NMR (400 MHz, CD$_3$OD) δ 8.83 (s, 1H), 7.96 (s, 1H), 7.80 (d, J = 8.3 Hz, 2H), 7.74 (d, J = 8.4 Hz, 2H), 4.66-4.56 (m, 1H), 4.53 (s, 2H), 3.91-3.58 (m, 9H), 3.55 (t, J = 7.1 Hz, 2H), 3.02 (s, 3H), 2.19-2.11 (m, 2H), 2.11-1.99 (m, 4H), 1.78-1.66 (m, 2H), 1.58-1.41 (m, 4H), 1.02 (t, J = 7.4 Hz, 3H); $^{13}$C NMR (101 MHz, CD$_3$OD) δ 154.6, 151.1, 138.7, 134.0, 132.1, 127.2, 127.0, 116.7, 110.0, 109.9, 68.5, 53.9, 50.0, 40.9, 33.7, 30.6, 29.5, 19.6, 12.7; MS m/z 477.35 [M + H]$^+$. |

TABLE 2-continued describes compounds prepared following procedures described in Example 2
(General Procedure B), using appropriate reagents. (Note: Mer IC50: ++++ means <10 nM;
+++ means between 10-100 nM, ++ means between 100 nM-1 µM; + means between 1-30 µM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 5 | 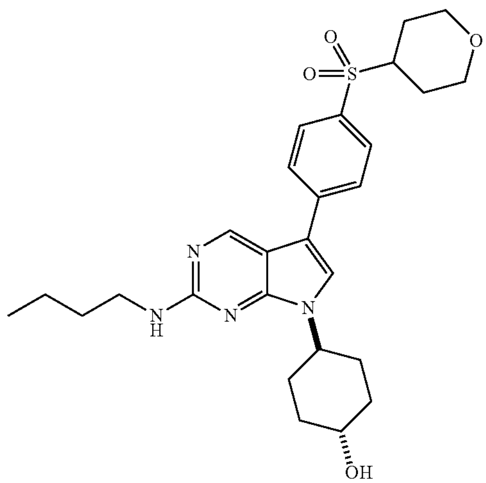 | UNC2026A | ++++ | $^1$H NMR (400 MHz, CD$_3$OD) δ 8.85 (s, 1H), 8.02 (s, 1H), 7.94-7.84 (m, 4H), 4.65-4.55 (m, 1H), 3.98 (dd, J = 11.5, 3.9 Hz, 2H), 3.78-3.67 (m, 1H), 3.54 (t, J = 7.1 Hz, 2H), 3.43-3.26 (m, 5H), 2.20-2.00 (m, 6H), 1.84 (d, J = 10.7 Hz, 2H), 1.77-1.64 (m, 4H), 1.59-1.42 (m, 4H), 1.02 (t, J = 7.4 Hz, 3H); MS m/z 513.30 [M + H]$^+$. |
| 6 | 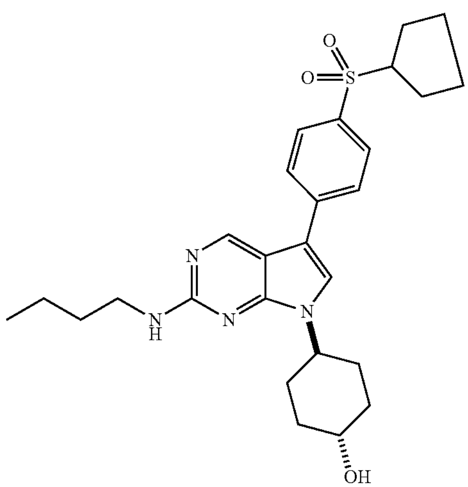 | UNC2087A | ++++ | $^1$H NMR (400 MHz, CD$_3$OD) δ 8.86 (s, 1H), 8.07 (s, 1H), 8.01-7.95 (m, 2H), 7.95-7.88 (m, 2H), 4.68-4.57 (m, 1H), 3.77-3.67 (m, 2H), 3.56 (t, J = 7.1 Hz, 2H), 2.20-1.97 (m, 8H), 1.95-1.85 (m, 2H), 1.79-1.62 (m, 6H), 1.58-1.43 (m, 4H), 1.07-0.98 (m, 3H); MS m/z 497.30 [M + H]$^+$. |
| 7 | 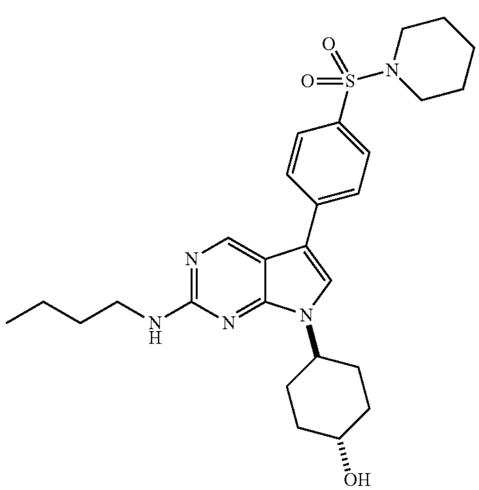 | UNC2078A | ++++ | $^1$H NMR (400 MHz, CD$_3$OD) δ 8.85 (s, 1H), 8.04 (s, 1H), 7.92-7.86 (m, 2H), 7.86-7.80 (m, 2H), 4.66-4.57 (m, 1H), 3.77-3.68 (m, 1H), 3.56 (t, J = 7.1 Hz, 2H), 3.06-2.94 (m, 4H), 2.19-1.98 (m, 6H), 1.78-1.68 (m, 2H), 1.68-1.60 (m, 4H), 1.59-1.38 (m, 6H), 1.03 (t, J = 7.4 Hz, 3H); MS m/z 512.30 [M + H]$^+$. |

TABLE 2-continued describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; – means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 8 | 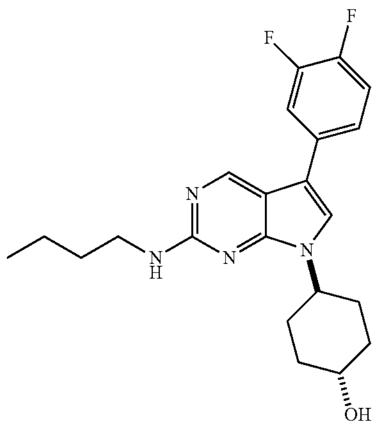 | UNC2094A | ++++ | $^1$H NMR (400 MHz, CD$_3$OD) δ 8.76 (s, 1H), 7.87 (s, 1H), 7.63-7.55 (m, 1H), 7.48-7.42 (m, 1H), 7.40-7.32 (m, 1H), 4.65-4.52 (m, 1H), 3.76-3.66 (m, 1H), 3.55 (t, J = 7.1 Hz, 2H), 2.19-1.98 (m, 6H), 1.75-1.66 (m, 2H), 1.59-1.44 (m, 4H), 1.02 (t, J = 7.4 Hz, 3H); MS m/z 401.20 [M + H]$^+$. |
| 9 | 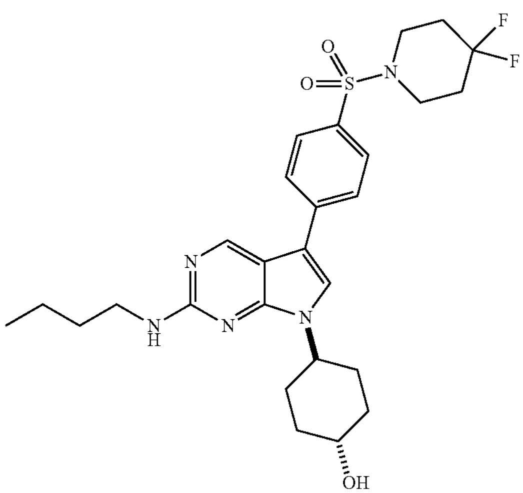 | UNC2095A | ++++ | $^1$H NMR (400 MHz, CD$_3$OD) δ 8.85 (s, 1H), 8.04 (s, 1H), 7.93-7.85 (m, 4H), 4.67-4.52 (m, 1H), 3.78-3.64 (m, 1H), 3.55 (t, J = 7.2 Hz, 2H), 3.26-3.19 (m, 4H), 2.21-1.95 (m, 10H), 1.75-1.68 (m, 2H), 1.57-1.44 (m, 4H), 1.03 (t, J = 7.4 Hz, 3H); MS m/z 548.25 [M + H]$^+$. |
| 10 | 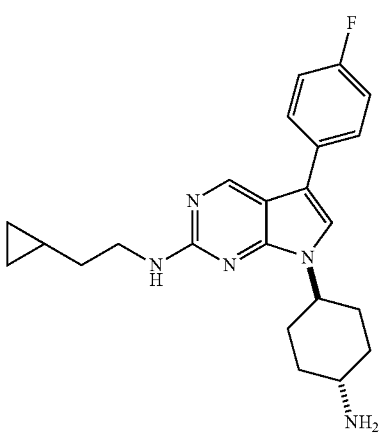 | UNC2123A | ++++ | $^1$H NMR (400 MHz, CD$_3$OD) δ 8.62 (s, 1H), 7.64 (s, 1H), 7.57-7.48 (m, 2H), 7.13-7.03 (m, 2H), 4.59-4.44 (m, 1H), 3.54-3.45 (m, 2H), 3.20-3.11 (m, 1H), 2.20-1.92 (m, 6H), 1.64-1.40 (m, 4H), 0.75-0.61 (m, 1H), 0.44-0.32 (m, 2H), 0.07-0.08 (m, 2H); MS m/z 394.25 [M + H]$^+$. |

TABLE 2-continued describes compounds prepared following procedures described in Example 2
(General Procedure B), using appropriate reagents. (Note: Mer IC50: ++++ means <10 nM;
+++ means between 10-100 nM, ++ means between 100 nM-1 μM; + means between 1-30 μM; – means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 11 | 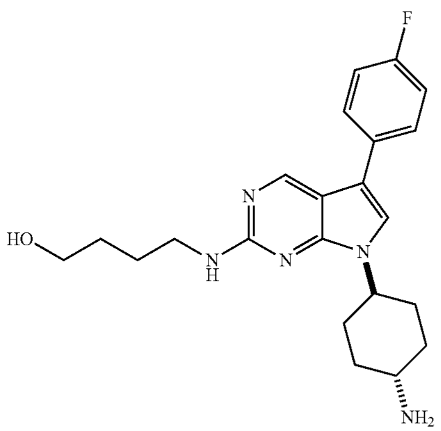 | UNC2124A | ++++ | $^1$H NMR (400 MHz, CD$_3$OD) δ 8.75 (d, J = 4.9 Hz, 1H), 7.77 (d, J = 1.4 Hz, 1H), 7.70-7.59 (m, 2H), 7.26-7.14 (m, 2H), 4.70-4.61 (m, 1H), 4.48 (t, J = 6.3 Hz, 2H), 3.69-3.54 (m, 4H), 2.29-2.10 (m, 6H), 1.94-1.63 (m, 6H); MS m/z 398.30 [M + H]$^+$. |
| 12 | 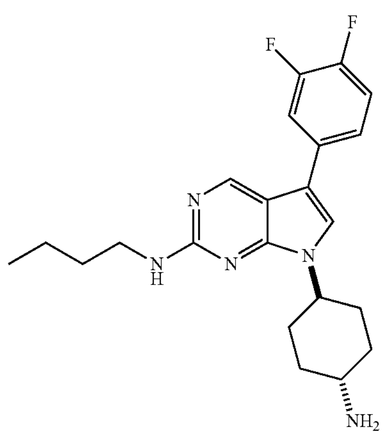 | UNC2125A | ++++ | $^1$H NMR (400 MHz, CD$_3$OD) δ 8.71 (s, 1H), 7.80 (s, 1H), 7.51 (ddd, J = 11.7, 7.6, 2.2 Hz, 1H), 7.41-7.35 (m, 1H), 7.32-7.24 (m, 1H), 4.61-4.52 (m, 1H), 3.46 (t, J = 7.1 Hz, 2H), 3.26-3.18 (m, 1H), 2.22-2.14 (m, 2H), 2.13-1.98 (m, 4H), 1.68-1.54 (m, 4H), 1.46-1.34 (m, 2H), 0.93 (t, J = 7.4 Hz, 3H); MS m/z 400.30 [M + H]$^+$. |
| 13 | 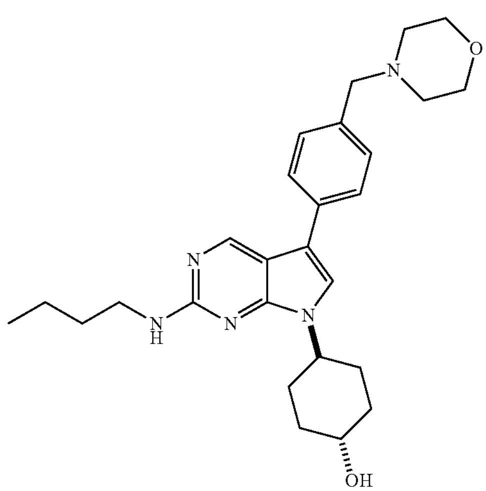 | UNC2142A | ++++ | $^1$H NMR (400 MHz, CD$_3$OD) δ 8.81 (s, 1H), 7.95 (s, 1H), 7.83-7.77 (m, 2H), 7.69-7.63 (m, 2H), 4.66-4.57 (m, 1H), 4.41 (s, 2H), 4.05 (d, J = 12.7 Hz, 2H), 3.84-3.69 (m, 3H), 3.55 (t, J = 7.1 Hz, 2H), 3.44-3.36 (m, 2H), 3.28-3.18 (m, 2H), 2.18-2.11 (m, 2H), 2.11-2.01 (m, 4H), 1.77-1.68 (m, 2H), 1.57-1.44 (m, 4H), 1.03 (t, J = 7.4 Hz, 3H); MS m/z 464.30 [M + H]$^+$. |

TABLE 2-continued

*describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; − means inactive.)*

| Structure | Compound_ID | Mer IC$_{50}$ | Physical Data MS m/z (M + 1) or/and $^1$H NMR (400 MHz, CD$_3$OD) |
|---|---|---|---|
| 14 | UNC2143A | ++++ | $^1$H NMR (400 MHz, CD$_3$OD) δ 8.81 (s, 1H), 7.95 (s, 1H), 7.82-7.76 (m, 2H), 7.75-7.69 (m, 2H), 4.65-4.57 (m, 1H), 4.48 (s, 2H), 3.77-3.69 (m, 1H), 3.66-3.50 (m, 10H), 2.20-2.03 (m, 6H), 1.77-1.67 (m, 2H), 1.58-1.45 (m, 4H), 1.03 (t, J = 7.4 Hz, 3H); MS m/z 463.30 [M + H]$^+$. |
| 15 | UNC2146A | ++++ | $^1$H NMR (400 MHz, CD$_3$OD) δ 8.87 (s, 1H), 8.09 (s, 1H), 8.00-7.92 (m, 4H), 4.66-4.58 (m, 1H), 4.22 (t, J = 12.3 Hz, 4H), 3.76-3.69 (m, 1H), 3.56 (t, J = 7.1 Hz, 2H), 2.21-2.00 (m, 6H), 1.76-1.68 (m, 2H), 1.60-1.45 (m, 4H), 1.03 (t, J = 7.4 Hz, 3H); MS m/z 520.20 [M + H]$^+$. |
| 16 | UNC2253A | ++++ | $^1$H NMR (400 MHz, cd3od) δ 8.83 (s, 1H), 7.96 (s, 1H), 7.80 (d, J = 8.1 Hz, 2H), 7.70 (d, J = 8.0 Hz, 2H), 4.66-4.55 (m, 1H), 3.92 (s, 4H), 3.80-3.62 (m, 2H), 3.56 (t, J = 7.2 Hz, 2H), 3.24-2.97 (m, 2H), 2.26-1.94 (m, 7H), 1.78-1.65 (m, 4H), 1.59-1.44 (m, 4H), 1.32 (t, J = 6.4 Hz, 2H), 1.03 (t, J = 7.4 Hz, 3H); MS m/z 490.30 [M + H]$^+$. |

TABLE 2-continued

*describes compounds prepared following procedures described in Example 2 (General Procedure B), using appropriate reagents. (Note: Mer IC50: ++++ means <10 nM; +++ means between 10-100 nM, ++ means between 100 nM-1 µM; + means between 1-30 µM; − means inactive.)*

| | Structure | Compound_ID | Mer IC$_{50}$ | Physical Data MS m/z (M + 1) or/and $^1$H NMR (400 MHz, CD$_3$OD) |
|---|---|---|---|---|
| 17 | 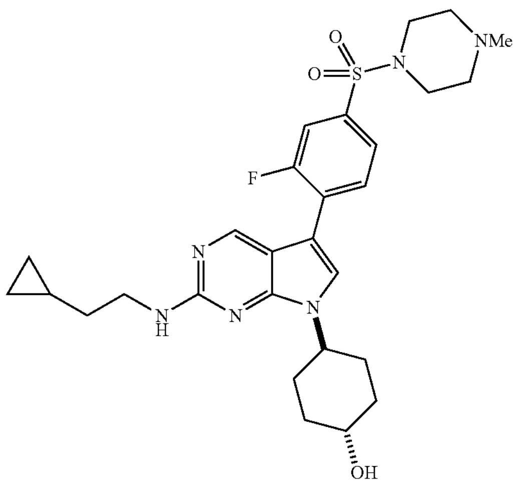 | UNC2367A | ++++ | $^1$H NMR (400 MHz, cd3od) δ 8.59 (d, J = 1.4 Hz, 1H), 7.85 (s, 1H), 7.81 (d, J = 8.0 Hz, 1H), 7.57-7.52 (m, 2H), 4.54-4.42 (m, 1H), 3.94-3.68 (m, 2H), 3.69-3.53 (m, 2H), 3.54-3.48 (m, 2H), 3.46-3.29 (m, 2H), 3.14-3.00 (m, 1H), 2.77 (s, 5H), 2.08-1.86 (m, 6H), 1.49 (dd, J = 14.3, 7.1 Hz, 2H), 1.46-1.33 (m, 2H), 0.73-0.63 (m, 1H), 0.41-0.34 (m, 2H), 0.02 (dd, J = 4.8, 1.2 Hz, 2H); MS m/z 557.30 [M + H]$^+$. |
| 18 | 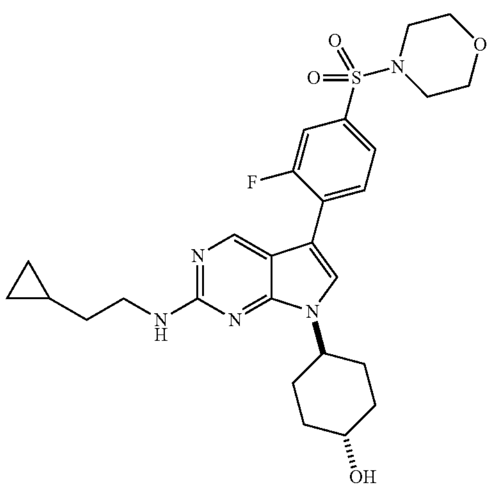 | UNC2368A | ++++ | $^1$H NMR (400 MHz, cd3od) δ 8.60 (d, J = 1.5 Hz, 1H), 7.85 (d, J = 0.6 Hz, 1H), 7.81-7.75 (m, 1H), 7.53 (s, 1H), 7.52-7.49 (m, 1H), 4.55-4.41 (m, 1H), 3.83 (s, 1H), 3.63-3.54 (m, 5H), 3.54-3.46 (m, 2H), 3.20 (s, 1H), 2.91-2.84 (m, 4H), 2.06-1.85 (m, 6H), 1.53-1.34 (m, 4H), 0.73-0.64 (m, 1H), 0.42-0.34 (m, 2H), 0.02 (d, J = 4.9 Hz, 2H); MS m/z 544.30 [M + H]$^+$. |
| 19 | 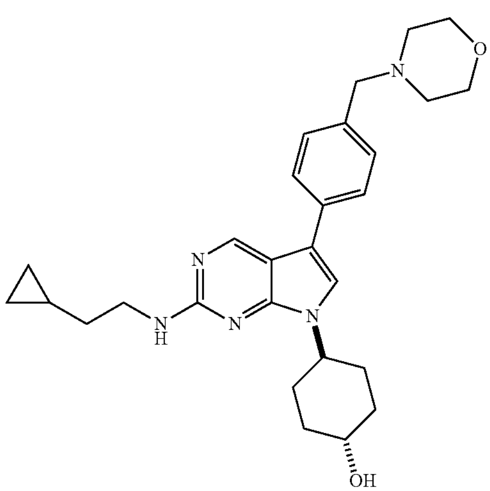 | UNC2370A | ++++ | $^1$H NMR (400 MHz, cd3od) δ 8.67 (s, 1H), 7.79 (s, 1H), 7.67-7.60 (m, 2H), 7.52-7.46 (m, 2H), 4.52-4.42 (m, 1H), 4.26 (s, 2H), 3.97-3.85 (m, 2H), 3.71-3.55 (m, 3H), 3.54-3.45 (m, 2H), 3.33-3.20 (m, 2H), 3.14-3.01 (m, 2H), 2.06-1.98 (m, 2H), 1.97-1.84 (m, 4H), 1.53-1.45 (m, 2H), 1.45-1.33 (m, 2H), 0.74-0.62 (m, 1H), 0.42-0.33 (m, 2H), 0.06-0.03 (m, 2H); MS m/z 476.30 [M + H]$^+$. |

TABLE 2-continued

*describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; − means inactive.)*

| | Structure | Compound_ID | Mer IC$_{50}$ | Physical Data MS m/z (M + 1) or/and $^1$H NMR (400 MHz, CD$_3$OD) |
|---|---|---|---|---|
| 20 | 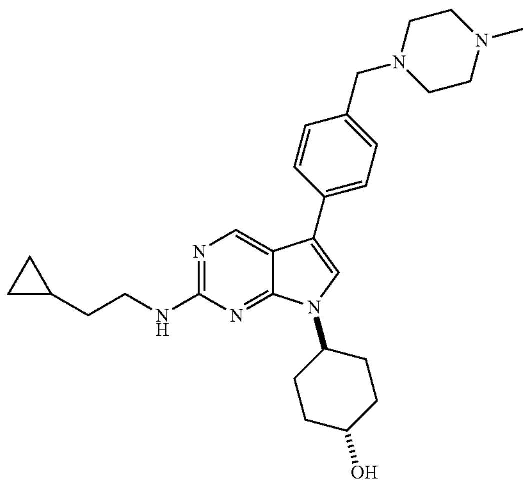 | UNC2371A | ++++ | $^1$H NMR (400 MHz, cd3od) δ 8.58 (s, 1H), 7.47 (d, J = 8.2 Hz, 2H), 7.28-7.21 (m, 3H), 4.48-4.36 (m, 1H), 3.66-3.53 (m, 1H), 3.47-3.37 (m, 4H), 2.53-2.29 (m, 6H), 2.19 (s, 3H), 2.06-1.97 (m, 2H), 1.96-1.81 (m, 4H), 1.50-1.34 (m, 4H), 1.23-1.09 (m, 1H), 0.90-0.63 (m, 2H), 0.42-0.34 (m, 2H), 0.06-0.03 (m, 2H); MS m/z 489.40 [M + H]$^+$. |
| 21 | 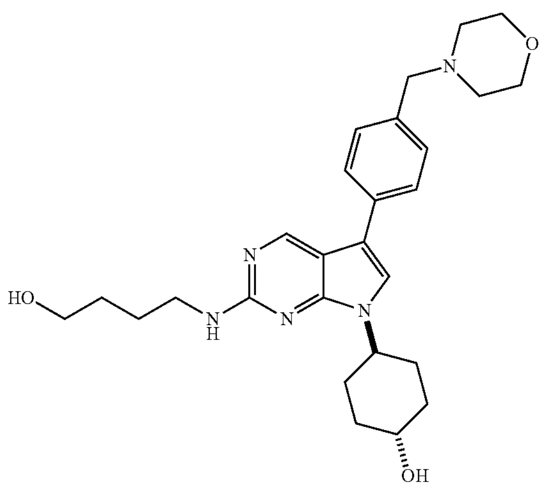 | UNC2395A | | $^1$H NMR (400 MHz, cd3od) δ 8.80 (s, 1H), 7.93 (s, 1H), 7.81-7.74 (m, 2H), 7.62 (d, J = 8.3 Hz, 2H), 4.68-4.56 (m, 1H), 4.40 (s, 2H), 4.11-3.95 (m, 2H), 3.83-3.68 (m, 3H), 3.68-3.54 (m, 4H), 3.50-3.35 (m, 2H), 3.29-3.16 (m, 2H), 2.20-1.99 (m, 7H), 1.88-1.76 (m, 2H), 1.74-1.63 (m, 2H), 1.60-1.45 (m, 2H); MS m/z 480.30 [M + H]$^+$. |
| 22 | 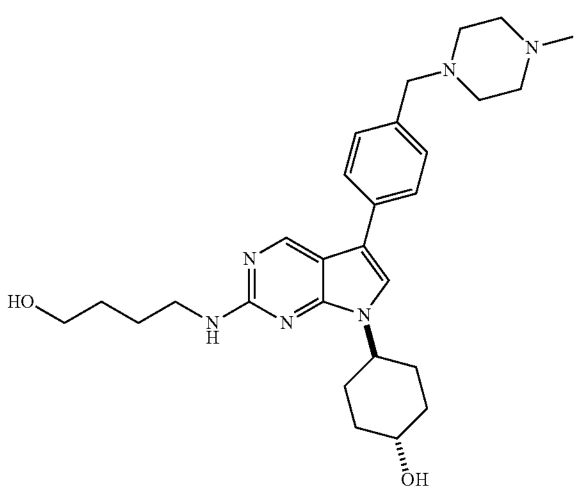 | UNC2396A | | $^1$H NMR (400 MHz, cd3od) δ 8.77 (s, 1H), 7.88 (d, J = 4.2 Hz, 1H), 7.71 (d, J = 8.3 Hz, 2H), 7.56 (d, J = 8.3 Hz, 2H), 4.65-4.56 (m, 1H), 4.16 (s, 2H), 3.79-3.67 (m, 1H), 3.67-3.62 (m, 2H), 3.62-3.55 (m, 2H), 3.50 (s, 4H), 3.29-3.24 (m, 1H), 2.93 (s, 3H), 2.26-1.91 (m, 7H), 1.86-1.73 (m, 2H), 1.73-1.63 (m, 2H), 1.60-1.46 (m, 2H); MS m/z 493.40 [M + H]$^+$. |

TABLE 2-continued describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 23 | 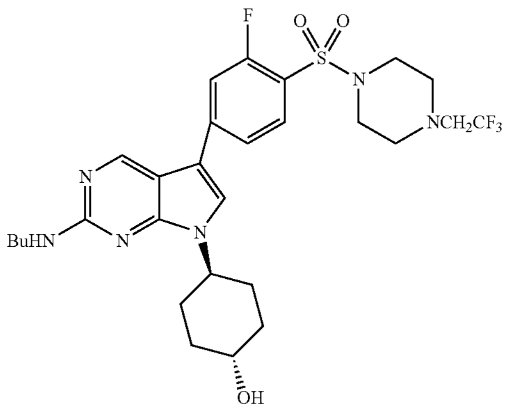 | UNC1651A | ++++ | $^1$H NMR (400 MHz, CD$_3$OD) δ 8.92 (s, 1H), 8.14 (s, 1H), 7.88 (t, J = 6.6 Hz, 1H), 7.76-7.63 (m, J = 10.8 Hz, 2H), 4.68-4.55 (d, J = 10.7 Hz, 1H), 3.80-3.68 (m, 1H), 3.61-3.49 (m, 4H), 3.36 (bs, 4H), 3.09 (bs, 4H), 2.21-1.99 (m, 6H), 1.79-1.67 (m, 2H), 1.59-1.45 (m, 4H), 1.03 (t, J = 7.3 Hz, 3H); MS m/z 613.3 [M + H]$^+$. |
| 24 | 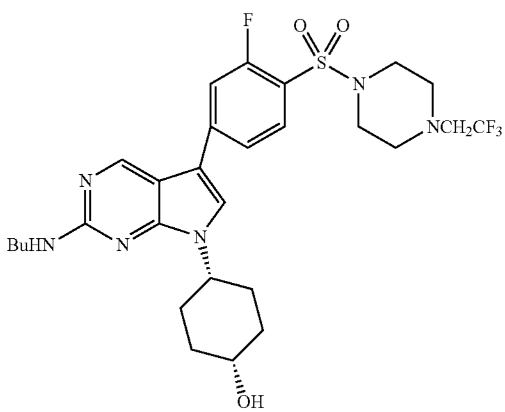 | UNC1652A | ++++ | $^1$H NMR (400 MHz, CD$_3$OD) δ 8.91 (s, 1H), 8.14 (s, 1H), 7.90 (t, J = 8.0 Hz, 1H), 7.77-7.68 (m, 2H), 4.66 (tt, J = 12.0, 3.7 Hz, 1H), 4.09 (bs, 1H), 3.57 (t, J = 7.1 Hz, 2H), 3.40 (q, J = 9.6 Hz, 2H), 3.34-3.31 (m, 4H), 3.03-2.92 (m, 4H), 2.42-2.26 (m, 2H), 2.01 (d, J = 14.9 Hz, 2H), 1.91-1.67 (m, 6H), 1.49 (dq, J = 14.5, 7.3 Hz, 2H), 1.02 (t, J = 7.4 Hz, 3H); MS m/z 613.2 [M + H]$^+$. |
| 25 | 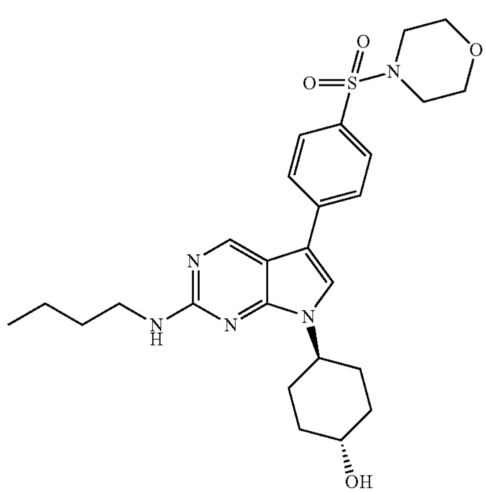 [SMILES: CCCCNc1ncc2c(-c3ccc(S(=O)(=O)N4CCOCC4)cc3)cn([C@H]3CC[C@H](O)CC3)c2n1] | UNC1666A | ++++ | $^1$H NMR (400 MHz, CD$_3$OD) δ 9.23 (s, 1H), 8.03 (dd, J = 8.7, 5.3 Hz, 2H), 7.30 (t, J = 8.7 Hz, 2H), 4.27 (d, J = 6.5 Hz, 2H), 3.86-3.51 (m, 9H), 3.46-3.35 (m, 1H), 2.27 (d, J = 11.0 Hz, 2H), 2.14 (bs, 1H), 1.98 (d, J = 12.8 Hz, 2H), 1.76-1.68 (m, 2H), 1.41-1.60 (m, 1H), 1.54-1.42 (m, 2H), 1.41-1.30 (m, 2H), 1.02 (t, J = 7.3 Hz, 3H); MS m/z 514.3 [M + H]$^+$. |

TABLE 2-continued describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; – means inactive.)

| Structure | Compound_ID | Mer IC$_{50}$ | Physical Data MS m/z (M + 1) or/and $^1$H NMR (400 MHz, CD$_3$OD) |
|---|---|---|---|
| 26 | UNC1667A | ++++ | $^1$H NMR (400 MHz, CD$_3$OD) δ 8.91 (s, 1H), 8.10 (s, 1H), 7.95 (d, J = 8.5 Hz, 2H), 7.89 (d, J = 8.5 Hz, 2H), 4.68-4.56 (m, 1H), 3.95 (bs, 2H), 3.79-3.68 (m, 1H), 3.66-3.50 (m, 4H), 3.30-3.14 (m, 2H), 2.90 (s, 3H), 2.83 (bs, 2H), 2.21-2.03 (m, 6H), 1.78-1.67 (m, 2H), 1.61-1.43 (m, 4H), 1.03 (t, J = 7.4 Hz, 3H); MS m/z 527.3 [M + H]$^+$. |
| 27 | UNC1668A | ++++ | $^1$H NMR (400 MHz, CD$_3$OD) δ 8.78 (s, 1H), 7.85 (s, 1H), 7.48 (t, J = 2.1 Hz, 1H), 7.45 (s, 1H), 7.28 (t, J = 8.5 Hz, 1H), 4.64-4.53 (m, 1H), 3.94-3.87 (m, 4H), 3.78-3.68 (m, 1H), 3.55 (t, J = 7.1 Hz, 2H), 3.27-3.21 (m, 4H), 2.19-2.10 (m, 2H), 2.10-2.02 (m, 4H), 1.77-1.67 (m, 2H), 1.58-1.44 (m, 4H), 1.03 (t, J = 7.4 Hz, 3H).; MS m/z 468.3 [M + H]$^+$. |
| 28 | UNC1669A | ++++ | $^1$H NMR (400 MHz, CD$_3$OD) δ 8.94 (s, 1H), 8.16 (s, 1H), 7.95-7.86 (m, 1H), 7.77-7.68 (m, 2H), 4.67-4.55 (m, 1H), 4.13-3.92 (bs, 2H), 3.78-3.68 (m, 1H), 3.68-3.49 (m, 4H), 3.30-3.19 (bs, 2H), 3.18-3.02 (bs, 2H), 2.93 (s, 3H), 2.21-2.01 (m, 6H), 1.78-1.66 (m, 2H), 1.60-1.43 (m, 4H), 1.03 (t, J = 7.4 Hz, 3H).; MS m/z 545.3 [M + H]$^+$. |

TABLE 2-continued describes compounds prepared following procedures described in Example 2 (General Procedure B), using appropriate reagents. (Note: Mer IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 29 | 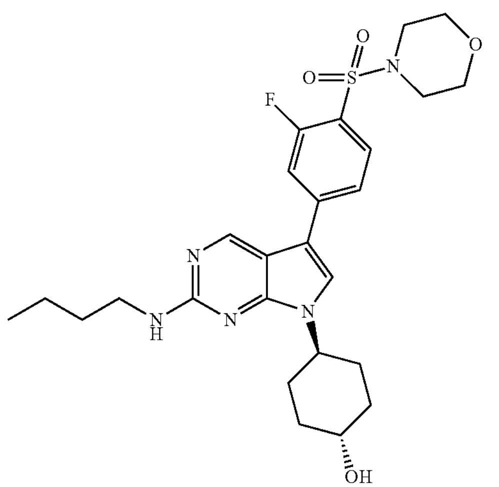 [SMILES: CCCCNc1ncc2c(-c3ccc(S(=O)(=O)N4CCOCC4)c(F)c3)cn([C@H]3CC[C@H](O)CC3)c2n1] | UNC1670A | ++++ | $^1$H NMR (400 MHz, CD$_3$OD) δ 8.91 (s, 1H), 8.13 (s, 1H), 7.91-7.83 (m, 1H), 7.73-7.64 (m, 2H), 4.66-4.57 (m, 1H), 3.79-3.67 (m, 5H), 3.56 (t, J = 7.1 Hz, 2H), 3.19-3.11 (m, 4H), 2.20-2.01 (m, 6H), 1.78-1.68 (m, 2H), 1.60-1.44 (m, 4H), 1.03 (t, J = 7.4 Hz, 3H).; MS m/z 532.2 [M + H]$^+$. |
| 30 | 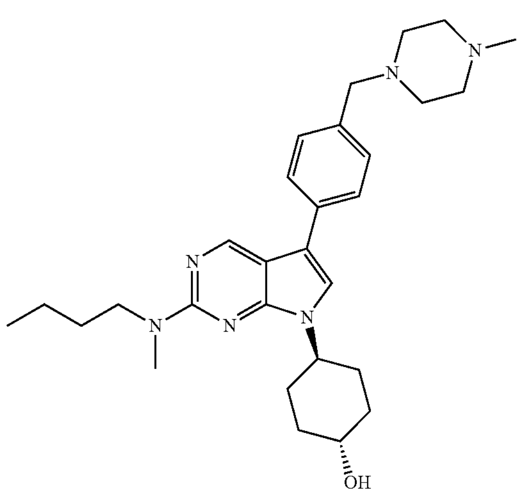 [SMILES: CCCCN(C)c1ncc2c(-c3ccc(CN4CCN(C)CC4)cc3)cn([C@H]3CC[C@H](O)CC3)c2n1] | UNC2369A | ++ | $^1$H NMR (400 MHz, CD$_3$OD) δ 8.63 (s, 1H), 7.88 (s, 1H), 7.71 (d, J = 8 Hz, 2H), 7.63 (d, J = 8 Hz, 2H), 4.53-4.38 (m, 1 H), 4.38 (s, 2H), 3.72-3.56 (m, 8H), 3.50 (s, 3H), 2.92 (s, 3H), 2.06-1.97 (m, 6H), 1.67-1.63 (m, 3H), 1.42-1.34 (m, 5H), 0.93 (t, J = 8 Hz, 3H). MS m/z 491.0 [M + H]$^+$. |

Example 3
Cis- and Trans-(1r,4r)-4-(2-(butylamino)-5-(4-fluorophenyl)-5H-pyrrolo[3,2-d]pyrimidin-7-yl)cyclohexanol
General Procedure C
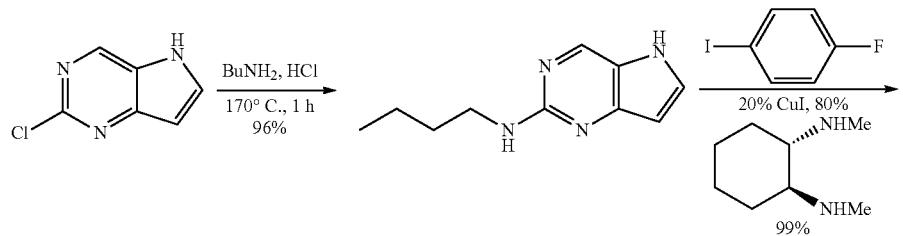
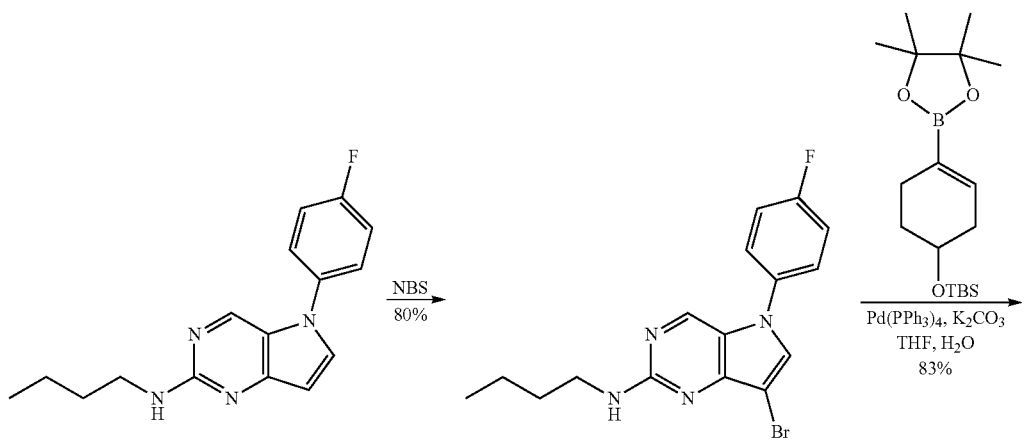
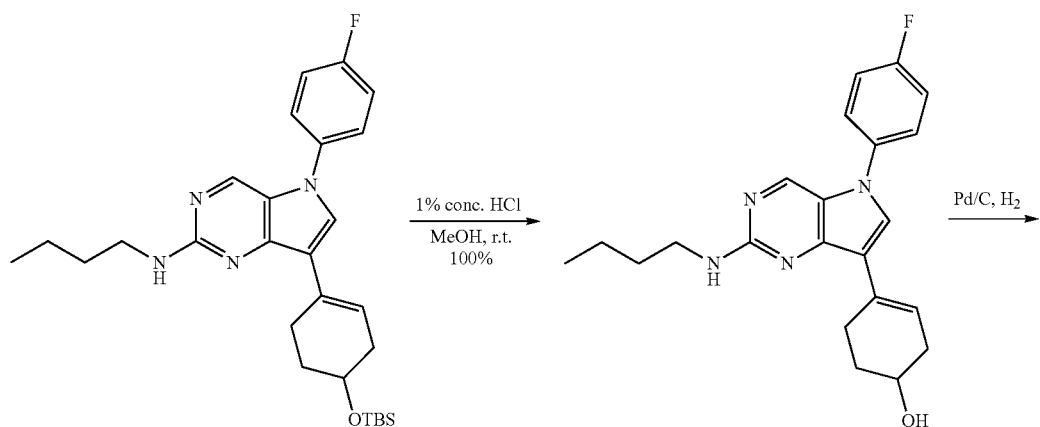

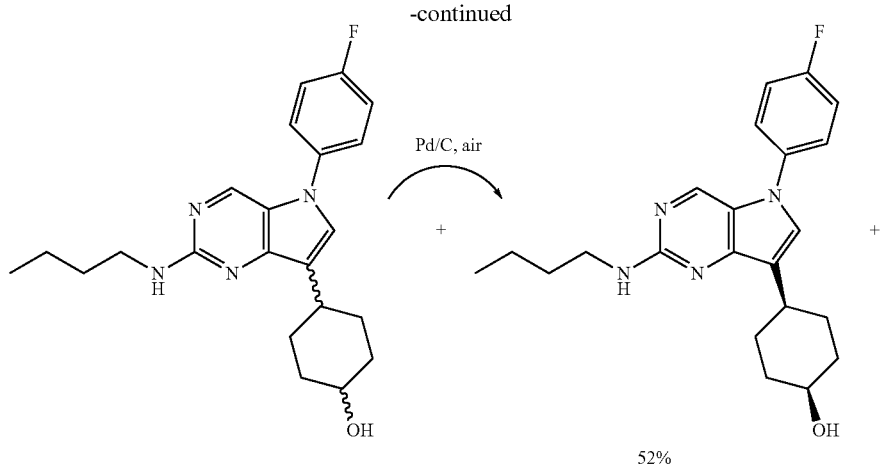

52%

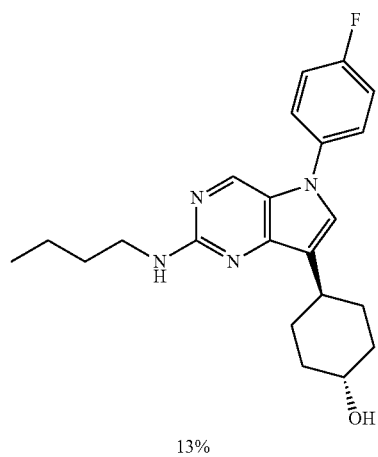 [SMILES: CCCCNc1ncc2c(n1)c([C@H]1CC[C@H](O)CC1)cn2-c1ccc(F)cc1]

13%

N-Butyl-5H-pyrrolo[3,2-d]pyrimidin-2-amine

N-Butyl-5-(4-fluorophenyl)-5H-pyrrolo[3,2-d]pyrimidin-2-amine

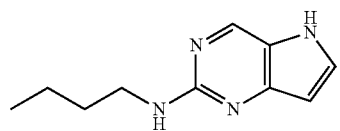

A suspension of 2-chloro-5H-pyrrolo[3,2-d]pyrimidine (0.62 g, 4 mmol) in 5 mL iPrOH was added nBuNH$_2$ (2.5 mL, 25.3 mmol) and followed by HCl (2.0 mL, 4.0 M in dioxanes, 8 mmol). The resulting solution was heated at 170° C. for 1h under microwave irradiation. The reaction was monitored by LC-MS. The reaction time should be extended whenever it is necessary. After evaporation of solvents, the crude product was washed with minimal amount of MeOH. The solid was collected. And the MeOH filtrate was purified by ISCO to provide the desired product (0.73 g, 96%). $^1$H NMR (400 MHz, CD$_3$OD) δ 8.42 (d, J=0.8 Hz, 1H), 7.53 (d, J=3.1 Hz, 1H), 6.27 (dd, J=3.0, 0.8 Hz, 1H), 3.37 (t, J=7.1 Hz, 2H), 1.68-1.57 (m, 2H), 1.52-1.36 (m, 2H), 0.97 (t, J=7.4 Hz, 3H); MS m/z 191.2 [M+H]$^+$.

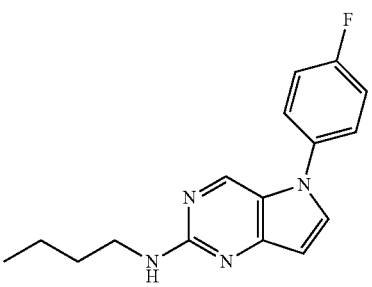 [SMILES: CCCCNc1ncc2c(ccn2-c2ccc(F)cc2)n1]

A mixture of N-butyl-5H-pyrrolo[3,2-d]pyrimidin-2-amine (0.73 g, 3.85 mmol), CuI (0.074 g, 0.39 mmol), and K$_3$PO$_4$ (1.63 g, 7.7 mmol) was added DMF (10 mL), 4-fluoroiodobenzene (0.54 mL, 4.62 mmol), and N,N'-dimethylcyclohexane-1,2-diamine (0.24 mL, 1.54 mmol) under Argon atmosphere. The mixture was heated at 110° C. for 16 h, then was filtered through a plug of celite at room temperature and washed with MeOH. The filtrate was concentrated and purified by ISCO to provide desired product (1.079 g, 99%). MS m/z 285.2 [M+H]$^+$.

7-Bromo-N-butyl-5-(4-fluorophenyl)-5H-pyrrolo[3,2-d]pyrimidin-2-amine

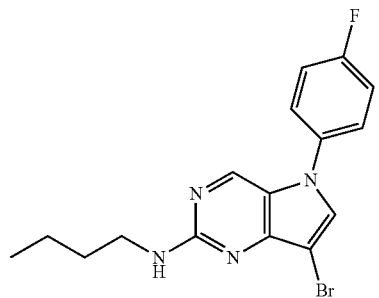 [SMILES: CCCCNc1ncc2c(n1)c(Br)cn2-c1ccc(F)cc1]

A solution of N-butyl-5-(4-fluorophenyl)-5H-pyrrolo[3,2-d]pyrimidin-2-amine (1.03 g, 3.61 mmol) in DMF (10 mL) was added NBS (0.71 g, 3.97 mmol) at room temperature.

The resulting solution was stirred for 1 h and diluted with EtOAc. The resulting solution was washed with a sat. aq. solution of NaHCO$_3$, H$_2$O and brine. The EtOAc layer was dried (Na$_2$SO$_4$), concentrated and purified by ISCO to provide the desired product (1.05 g, 80%). $^1$H NMR (400 MHz, CD$_3$OD) δ 8.46 (s, 1H), 7.68 (s, 1H), 7.52-7.42 (m, 2H), 7.32-7.21 (m, 2H), 3.44 (t, J=7.1 Hz, 2H), 1.68-1.54 (m, 2H), 1.49-1.36 (m, 2H), 0.95 (t, J=7.3 Hz, 3H); MS m/z 363.1 [M+H]$^+$.

N-Butyl-7-(4-(tert-butyldimethylsilyloxy)cyclohex-1-enyl)-5-(4-fluorophenyl)-5H-pyrrolo[3,2-d]pyrimidin-2-amine

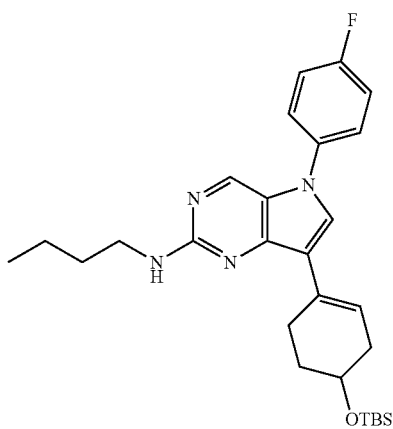 [SMILES: CCCCNc1ncc2c(n1)c(C1=CCC(O[Si](C)(C)C(C)(C)C)CC1)cn2-c1ccc(F)cc1]

A mixture of 7-bromo-N-butyl-5-(4-fluorophenyl)-5H-pyrrolo[3,2-d]pyrimidin-2-amine (0.11 g, 0.3 mmol), tert-butyldimethyl(4-(4,4,5,5-tetramethyl-1,3,2-dioxaborolan-2-yl)cyclohex-3-enyloxy)silane (0.15 g, 0.45 mmol), potassium phosphonate (0.083 g, 0.60 mmol), tetrakis(triphenylphosphine)palladium (0.035 g, 0.03 mmol) in THF (4 mL) and water (1 mL) was stirred at room temperature for 1 min, then was heat at 150° C. for 1 h under microwave irradiation. The reaction mixture was diluted with EtOAc and washed with water. The aqueous layer was extracted with EtOAc (3X). The combined organic layer was dried (Na$_2$SO$_4$), concentrated, and purified by ISCO to provide the desired product (0.12 g, 83%). $^1$H NMR (400 MHz, CDCl$_3$) δ 8.48 (s, 1H), 7.41-7.34 (m, 2H), 7.32 (s, 1H), 7.20 (t, J=8.5 Hz, 2H), 7.17-7.12 (m, 1H), 4.97 (t, J=5.6 Hz, 1H), 4.09-3.95 (m, 1H), 3.49 (dd, J=13.3, 6.5 Hz, 2H), 2.68-2.44 (m, 3H), 2.35-2.23 (m, 1H), 2.03-1.94 (m, 1H), 1.86-1.74 (m, 1H), 1.72-1.59 (m, 2H), 1.52-1.39 (m, 2H), 0.97 (t, J=7.3 Hz, 3H), 0.92 (s, 9H), 0.10 (s, 6H); MS m/z 495.3 [M+H]$^+$.

4-(2-(Butylamino)-5-(4-fluorophenyl)-5H-pyrrolo[3,2-d]pyrimidin-7-yl)cyclohex-3-enol

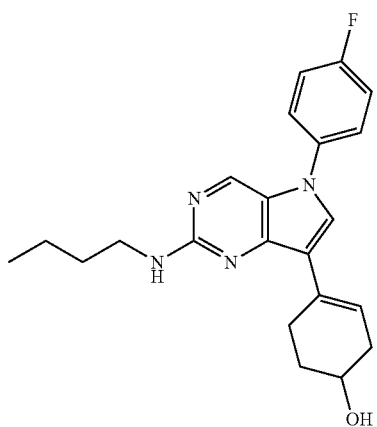 [SMILES: CCCCNc1ncc2c(n1)c(C1=CCC(O)CC1)cn2-c1ccc(F)cc1]

A solution of N-butyl-7-(4-(tert-butyldimethylsilyloxy)cyclohex-1-enyl)-5-(4-fluorophenyl)-5H-pyrrolo[3,2-d]pyrimidin-2-amine (0.12 g, 0.25 mmol) in EtOH (5 mL) was added 2 drops of concentrated HCl solution. The resulting reaction mixture was stirred at room temperature for 16 h and concentrated to give the desired product use as such. $^1$H NMR (400 MHz, CD$_3$OD) δ 8.59 (s, 1H), 8.23 (s, 1H), 7.66-7.58 (m, 2H), 7.40-7.31 (m, 2H), 6.88 (s, 1H), 4.05-3.93 (m, 1H), 3.54 (t, J=7.2 Hz, 2H), 2.77-2.66 (m, 1H), 2.63-2.51 (m, 2H), 2.28-2.16 (m, 1H), 2.11-1.99 (m, 1H), 1.85-1.75 (m, 1H), 1.75-1.65 (m, 2H), 1.54-1.40 (m, 2H), 1.01 (t, J=7.4 Hz, 3H); MS m/z 381.2 [M+H]$^+$.

Cis-and Trans-4-(2-(butylamino)-5-(4-fluorophenyl)-5H-pyrrolo[3,2-d]pyrimidin-7-yl)cyclohexanol

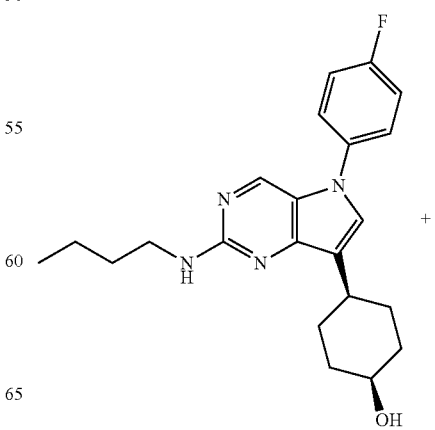

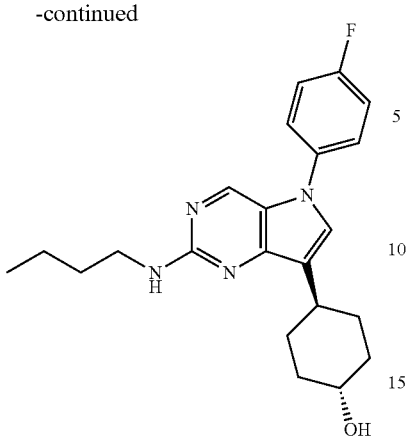

A mixture of 4-(2-(butylamino)-5-(4-fluorophenyl)-5H-pyrrolo[3,2-d]pyrimidin-7-yl)cyclohex-3-enol (0.095 g, 0.25 mmol) and Pd/C (0.01 g, 10 wt %) in 5 mL MeOH was stirred under H$_2$ atmosphere for 3 h. After filter through a plug of celite, the filtrate was concentrated and purified by Prep-HPLC. The cis-4-(2-(butylamino)-5-(4-fluorophenyl)-5H-pyrrolo[3,2-d]pyrimidin-7-yl)cyclohexanol was obtained as the major product (0.040 g). The trans-4-(2-(butylamino)-5-(4-fluorophenyl)-5H-pyrrolo [3,2-d]pyrimidin-7-yl)cyclohexanol was co-elute with 4-(2-(butylamino)-5-(4-fluorophenyl)-6,7-dihydro-5H-pyrrolo[3,2-d]pyrimidin-7-yl)cyclohexanol (0.035 g).

A solution of mixture of trans-4-(2-(butylamino)-5-(4-fluorophenyl)-5H-pyrrolo [3,2-d]pyrimidin-7-yl)cyclohexanol and 4-(2-(butylamino)-5-(4-fluorophenyl)-6,7-dihydro-5H-pyrrolo[3,2-d]pyrimidin-7-yl)cyclohexanol (0.035 g, ~0.091 mmol) in 5 mL MeOH was added Pd/C (0.004 g, 10 wt %). The mixture was stirred overnight under air. After filter through a plug of celite, the filtrate was concentrated and purified by ISCO to provide cis-4-(2-(butylamino)-5-(4-fluorophenyl)-5H-pyrrolo[3,2-d]pyrimidin-7-yl)cyclohexanol (0.010 g, 13% over 3 steps) and trans-4-(2-(butylamino)-5-(4-fluorophenyl)-5H-pyrrolo[3,2-d]pyrimidin-7-yl)cyclohexanol (0.012 g+0.040 g, 52% over 3 steps). Cis-isomer (UNC1861A): $^1$H NMR (400 MHz, CD$_3$OD) δ 8.47 (s, 1H), 7.55-7.49 (m, 3H), 7.32-7.25 (m, 2H), 4.06-3.99 (m, 1H), 3.43 (t, J=7.1 Hz, 2H), 2.97 (tt, J=10.6, 3.7 Hz, 1H), 2.06-1.96 (m, 2H), 1.93-1.82 (m, 4H), 1.79-1.68 (m, 2H), 1.68-1.59 (m, 2H), 1.49-1.39 (m, 2H), 0.97 (t, J=7.4 Hz, 3H); MS m/z 383.3 [M+H]$^+$. Trans-isomer (UNC1860A): $^1$H NMR (400 MHz, CD$_3$OD) δ 8.45 (s, 1H), 7.53-7.47 (m, 3H), 7.28 (t, J=8.7 Hz, 2H), 3.69-3.57 (m, 1H), 3.42 (t, J=7.1 Hz, 2H), 2.83 (tt, J=12.4, 3.2 Hz 1H), 2.20-2.13 (m, 2H), 2.11-2.02 (m, 2H), 1.73-1.58 (m, 4H), 1.53-1.39 (m, 4H), 0.98 (t, J =7.4 Hz, 3H); MS m/z 383.3 [M+H]$^+$.

Example 4

4-(2-(Butylamino)-5-(4-(morpholinomethyl)phenyl)-5H-pyrrolo[3,2-d]pyrimidin-7-yl)cyclohexanol General Procedure D:

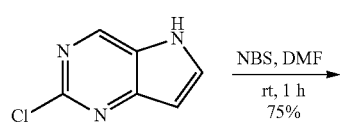

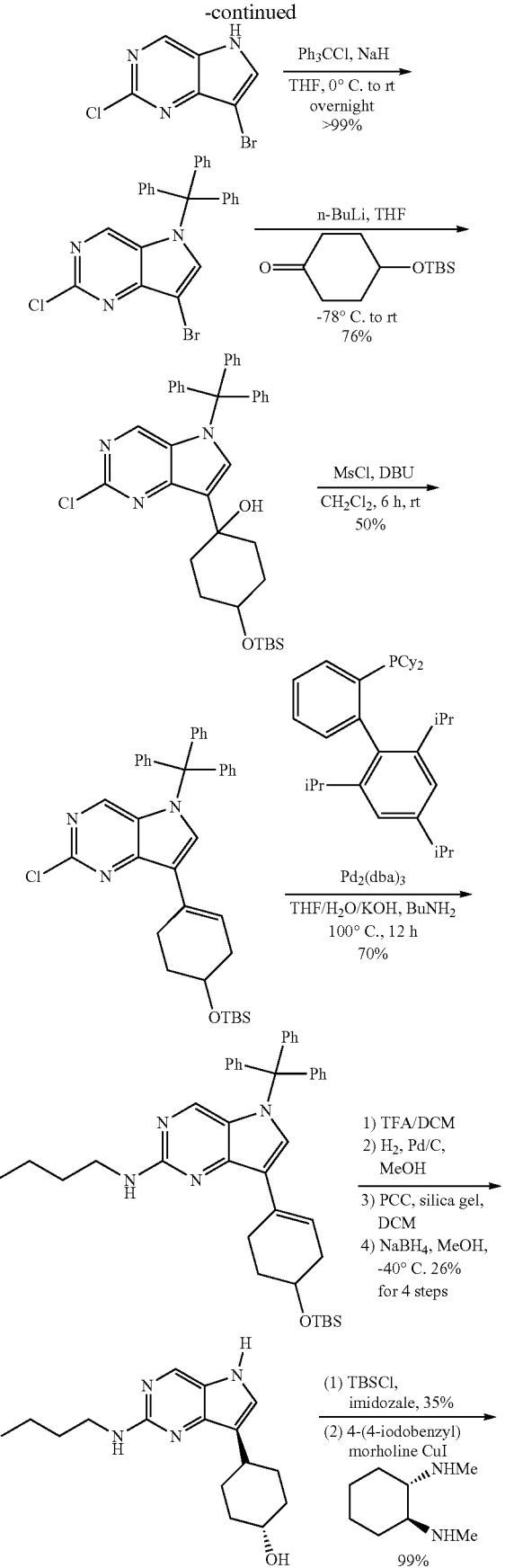

-continued

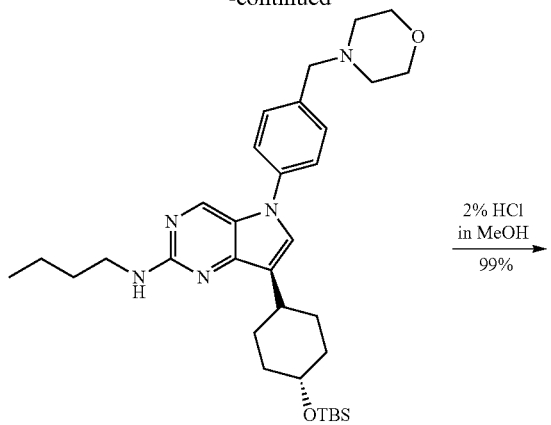

7-Bromo-2-chloro-5H-pyrrolo[3,2-d]pyrimidine

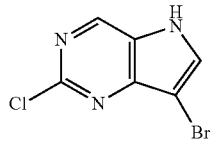 [SMILES: Clc1ncc2[nH]cc(Br)c2n1]

A solution of 2-chloro-5H-pyrrolo[3,2-d]pyrimidine (1.54 g, 10 mmol) in DMF (10 mL) was added NBS (2.00 g, 11 mmol) at room temperature. The resulting solution was stirred for 1 h and diluted with EtOAc. The resulting solution was washed with a sat. aq. solution of NaHCO$_3$, H$_2$O and brine. The EtOAc layer was dried (Na$_2$SO$_4$), concentrated and purified by ISCO to provide the desired product (1.75 g, 75%). $^1$H NMR (400 MHz, CD$_3$OD) δ 8.53 (s, 1H), 7.60 (s, 1H); MS m/z 234.0 [M+H]$^+$.

7-Bromo-2-chloro-5-trityl-5H-pyrrolo[3,2-d]pyrimidine

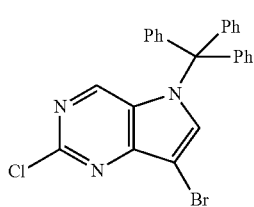 [SMILES: Clc1ncc2c(n1)c(Br)cn2C(c1ccccc1)(c1ccccc1)c1ccccc1]

A suspension of NaH (300 mg, 60% in mineral oil, 7.5 mmol) in THF (30 mL) was added a solution of 7-bromo-2-chloro-5H-pyrrolo[3,2-d]pyrimidine (1.16 g, 5.0 mmol) in THF (20 mL) dropwise at 0° C. After 20 min, a solution of TrCl (1.674 g, 6 mmol) in THF (10 mL) was added dropwise. The reaction mixture was stirred for 6 hours, quenched with brine and extracted with EtOAc (3x). The combined organic layer was dried (MgSO$_4$), filtered and concentrated. The residue was purified by ISCO to provide the desired product (2.38 g, >99%). $^1$H NMR (400 MHz, CD$_3$OD) δ 7.63 (s, 1H), 7.57 (s, 1H), 7.37-7.32 (m, 9H), 7.14-7.11 (m, 6H).

4-((tert-Butyldimethylsilyl)oxy)-1-(2-chloro-5-trityl-5H-pyrrolo[3,2-d]pyrimidin-7-yl)cyclohexanol

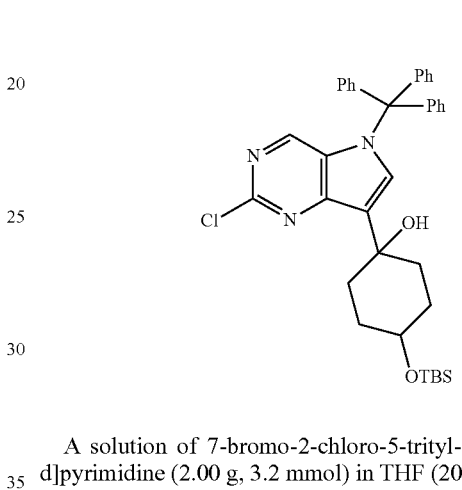

A solution of 7-bromo-2-chloro-5-trityl-5H-pyrrolo[3,2-d]pyrimidine (2.00 g, 3.2 mmol) in THF (20 mL) was added a 2.5 N solution of BuLi in hexane (2.82 mL, 7.04 mmol) at −78° C. Then 4-((tert-butyldimethylsilyl)oxy)cyclohexanone (1.2 mL) was added after 15 min. The reaction was stirred at −78° C. for 3 hour, quenched with brine and extracted with EtOAc (3x). The combined organic layer was dried (MgSO$_4$), filtered and concentrated. The residue was purified by ISCO to provide the desired product (1.52 g, 76%). $^1$H NMR (400 MHz, CDCl$_3$, two isomers) δ 7.64-7.56 (m, 1H), 7.44-7.41 (m, 1H), 7.35-7.31 (m, 9H), 7.16-7.10 (m, 6H), 3.73-3.68 (m, 1H), 2.55-2.51 (m, 1H), 2.42-2.30 (m, 1H), 2.28-2.19 (m, 1H), 2.07-1.94 (m, 2H), 1.91-1.82 (m, 2H), 1.76-1.62 (m, 2H), 0.82 (s, 9H), 0.01 (s, 6H).

7-(4-((tert-Butyldimethylsilyl)oxy)cyclohex-1-en-1-yl)-2-chloro-5-trityl-5H-pyrrolo[3,2-d]pyrimidine

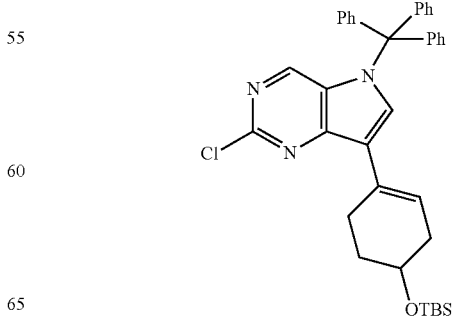

A solution of 4-((tert-butyldimethylsilyl)oxy)-1-(2-chloro-5-trityl-5H-pyrrolo[3,2-d]pyrimidin-7-yl)cyclohexanol (1.00 g, 1 6 mmol) in CH$_2$Cl$_2$ (20 mL) was added MsCl (275 mg, 2.4 mmol) followed by NEt$_3$ (808 mg, 8 mmol). The reaction mixture was stirred at room temperature for 6 hours, quenched with brine and extracted with EtOAc (3x). The combined organic layer was dried (MgSO$_4$), filtered and concentrated. The residue was purified by ISCO to provide the desired product (485 mg, 50%). $^1$H NMR (400 MHz, CDCl$_3$) δ 7.56 (s, 1H), 7.34 (s, 1H), 7.25-7.21 (m, 9H), 7.08-7.05 (m, 6H), 6.89 (s, 1H), 3.90-3.86 (m, 1H), 2.49-2.43 (m, 1H), 2.37-2.28 (m, 1H), 2.19-2.13 (m, 1H), 1.85-1.82 (m, 1H), 1.68-1.62 (m, 2H), 0.82 (s, 9H), 0.00 (s, 6H).

N-Butyl-7-(4-((tent-butyldimethylsilyl)oxy)cyclohex-1-en-1-yl)-5-trityl-5H-pyrrolo[3,2-d]pyrimidin-2-amine

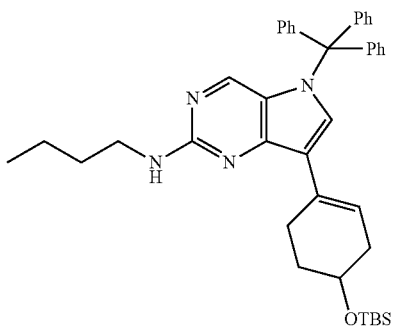 [SMILES: CCCCNc1ncc2c(n1)c(C1=CCC(O[Si](C)(C)C(C)(C)C)CC1)cn2C(c1ccccc1)(c1ccccc1)c1ccccc1]

A solution of 7-(4-((tert-butyldimethylsilyl)oxy)cyclohex-1-en-1-yl)-2-chloro-5-trityl-5H-pyrrolo[3,2-d]pyra-midine (485 mg, 0.8 mmol) in dioxane (3.0 mL) was added Pd$_2$(dba)$_3$ (73 mg, 0.08 mmol). The reaction mixture was stirred until the solution became clear. Then 2-dicyclohexylphosphino-2',4',6'-triisopropylbiphenyl (152 mg, 0.32 mmol) was added followed by the addition of water (4.0 mL) and potassium hydroxide (135 mg, 2.4 mmol). The reaction mixture was heated under reflux for 12 hours under Argon atmosphere, then cooled to room temperature. The reaction was diluted with EtOAc. The organic layer was dried (MgSO$_4$), filtered and concentrated. The residue was purified by ISCO to provide the desired product (360 mg, 70%). $^1$H NMR (400 MHz, CDCl$_3$) δ 7.40 (s, 1H), 7.30-7.28 (m, 9H), 7.19-7.15 (m, 7H), 7.07 (s, 1H), 3.98-3.92 (m, 1H), 3.42-3.37 (dd, J$_1$=12 Hz, J$_2$=8 Hz, 2H), 2.55-2.47 (m, 1H), 2.42-2.32 (m, 1H), 2.28-2.21 (m, 1H), 1.93-1.86 (m, 1H), 1.75-1.70 (m, 2H), 1.69-1.58 (m, 2H), 1.46-1.37 (m, 2H), 0.89 (t, J=4 Hz, 3H), 0.82 (s, 9H), 0.00 (s, 6H).

4-(2-(Butylamino)-5H-pyrrolo[3,2-d]pyrimidin-7-yl)cyclohexanol

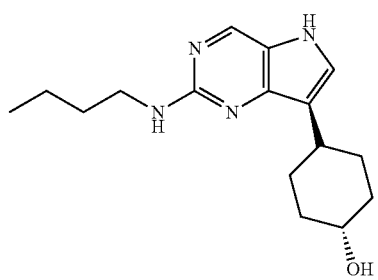

A solution of N-Butyl-7-(4-((tert-butyldimethylsilyl)oxy)cyclohex-1-en-1-yl)-5-trityl-5H-pyrrolo[3,2-d]pyrim-idin-2-amine (992 mg, 1.54 mmol) in CH$_2$Cl$_2$ (20 mL) was added trifluoroacetic acid (5.0 mL). The reaction mixture was stirred for 4 hours and quenched by a saturated aq. solution of NaHCO$_3$ and diluted with EtOAc. The organic layer was dried (MgSO$_4$), filtered and concentrated. The residue was dissolved in MeOH (6.0 mL) and Pd/C (44 mg) was added. The reaction mixture was then stirred under the hydrogen atmosphere for 12 hours and then filtered. The filtrate was concentrated to afford a brown residue. A solution of the residue in CH$_2$Cl$_2$ (10 mL) was added a mixture of PCC (665 mg, 3.084 mmol) and silica gel (668 mg). After 30 min, the reaction was quenched with water and extracted with EtOAc (3x). The combined organic layer was dried (MgSO$_4$), filtered and concentrated. The residue was purified by ISCO to provide the desired product 4-(2-(butylamino)-5H-pyrrolo[3,2-d]pyrimidin-7-yl)cyclohexanone (MS m/z 287.2 [M+H]$^+$). A solution of 4-(2-(butylamino)-5H-pyrrolo[3,2-d]pyrimidin-7-yl)cyclohexanone in MeOH (10 mL) was added NaBH$_4$ (67 mg, 1.71 mmol) slowly at −40° C. The reaction was quenched with water after 1 h and extracted with EtOAc (3x). The combined organic layer was dried (MgSO$_4$), filtered and concentrated. The residue was purified by ISCO to provide the desired product which was used without further purification. MS m/z 289.2 [M+H]$^+$.

N-Butyl-7-(4-((tert-butyldimethylsilyl)oxy)cyclohexyl)-5-(4-(morpholinomethyl)phenyl)-5H-pyrrolo[3,2-d]pyrimidin-2-amine

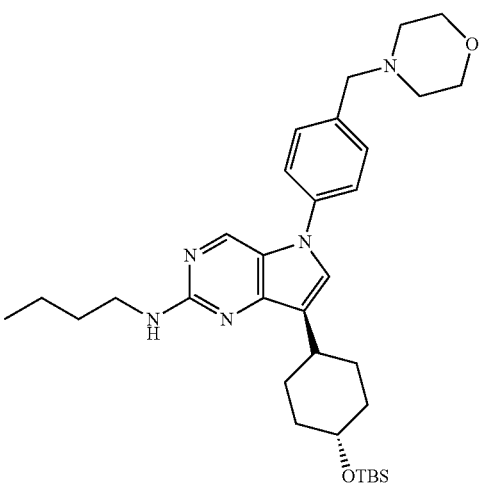

A solution of 4-(2-(butylamino)-5H-pyrrolo[3,2-d]pyrimidin-7-yl)cyclohexanol (122 mg, 0.423 mmol) and TBSCl (77 mg, 0.51 mmol) in THF (3 mL) was added imidazole (44 mg, 0.636 mmol). The reaction mixture was stirred for 6 hours, quenched with water and extracted with EtOAc (3x). The combined organic layer was dried (MgSO$_4$), filtered and concentrated. The residue was purified by ISCO to provide the desired product N-butyl-7-(4-((tert-butyldimethylsilyl)oxy)cyclohexyl)-5H-pyrrolo[3,2-d]pyrimidin-2-amine (59 mg, 0.14653 mmol). MS m/z 403.3 [M+H]$^+$.

A solution of N-butyl-7-(4-((tert-butyldimethylsilyl)oxy)cyclohexyl)-5H-pyrrolo[3,2-d]pyrimidin-2-amine (59 mg, 0.14653 mmol) and 4-iodobenzyl morpholine (67 mg, 0.22 mmol) in NMP (1 mL) was added CuI (3mg, 0.022 mmol) and N,N'-dimethylcyclohexane-1,2-diamine (2 mg, 0.044 mmol). The reaction mixture was stirred under microwave irradiation at 195° C. for 30 min. Then the reaction was diluted with EtOAc. The organic layer was dried (MgSO$_4$), filtered and concentrated. The residue was purified by ISCO to provide the desired product (85 mg, 99%). $^1$H NMR (400 MHz, CDCl$_3$) δ 8.48 (s, 1H), 7.36 (d, J=8 Hz, 2H), 7.25 (d, J=8 Hz, 2H), 7.17 (s, 1 H), 4.86 (s, 1H), 3.71-3.52 (m, 4H), 3.44-3.38 (m, 4H), 3.32-3.17 (m, 1H), 2.81-2.71 (m, 2H), 2.45-2.33 (m, 4H), 2.15-2.04 (m, 2H), 1.96-1.83 (m, 2H), 1.61-1.29 (m, 8H), 0.94-0.75 (m, 12 H), 0.00 (s, 6H). MS m/z 578.4 [M+H]$^+$.

4-(2-(Butylamino)-5-(4-(morpholinomethyl)phenyl)-5H-pyrrolo[3,2-d]pyrimidin-7-yl)cyclohexanol

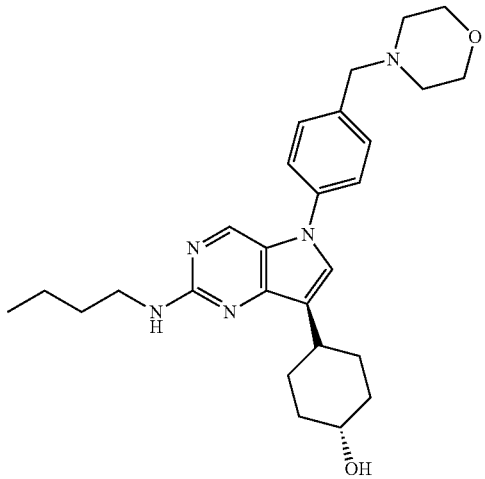

A solution of N-butyl-7-(4-((tert-butyldimethylsilyl)oxy)cyclohexyl)-5-(4-(morpholinomethyl)phenyl)-5H-pyrrolo[3,2-d]pyrimidin-2-amine (84 mg, 0.14653 mmol) in MeOH (3.0 mL) was added 0.15 mL of concentrated HCl. The reaction mixture was stirred overnight and the solvent was removed. The residue was purified by ISCO to provide the desired product (UNC2221A) (68 mg, 99%). $^1$H NMR (400 MHz, CD$_3$OD) δ 8.69 (s, 1H), 8.13 (s, 1H), 7.74 (d, J=8 Hz, 2H), 7.25 (d, J=8 Hz, 2H), 4.38 (s, 2 H), 4.01-3.92 (m, 2H), 3.80-3.70 (m, 2H), 3.59-3.52 (m, 2H), 3.48 (t, J=8 Hz, 2H), 3.37-3.29 (m, 2H), 3.18-3.11 (m, 1H), 2.78 (tt, J$_1$=12 Hz, J$_2$=4 Hz, 1H), 2.02 (t, J=16 Hz, 4H), 1.68-1.57 (m, 4H), 1.43-1.13 (m, 4H), 0.91 (t, J=8 Hz, 3H). MS m/z 464.3 [M+H]$^+$.

TABLE 3 describes compounds prepared following procedures described in Example 4 (General Procedure D), using appropriate reagents. (Note: Mer IC50: ++++ means <10 nM; +++ means between 10-100 nM, ++ means between 100 nM-1 μM; + means between 1-30 μM; − means inactive.)

| | Structure | Compound_ID | Mer IC$_{50}$ | Physical Data MS m/z (M + 1) or/and $^1$H NMR (400 MHz, CD$_3$OD) |
|---|---|---|---|---|
| 1 | 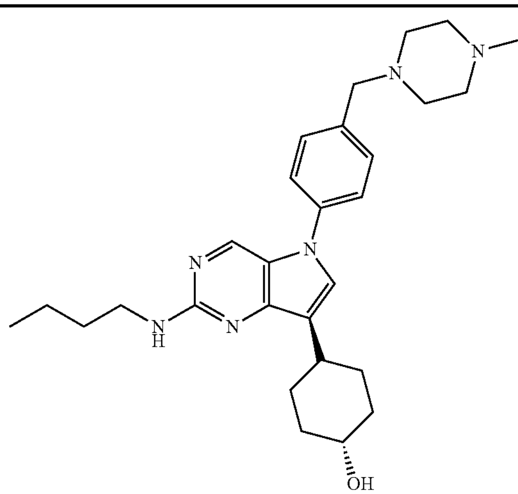 | UNC2421A | ++++ | $^1$H NMR (400 MHz, CD$_3$OD) δ 8.79 (s, 1H), 8.21 (s, 1H), 7.89 (d, J = 8 Hz, 2H), 7.71 (d, J = 8 Hz, 2H), 5.47 (s, 1H), 4.61 (s, 2H), 3.74-3.71 (m, 6H), 3.67-3.63 (m, 2H), 3.58-3.54 (m, 2H), 3.33 (s, 1H), 3.01 (s, 3H), 2.86 (t, J = 12 Hz, 1H), 2.65 (s, 1H), 2.13-2.06 (m, 4H), 1.70-1.67 (m, 4H), 1.47-1.45 (m, 4H), 0.98 (t, J = 8 Hz, 3H); MS m/z 477.0 [M + 1]$^+$. |

TABLE 3-continued describes compounds prepared following procedures described in Example 4 (General Procedure D), using appropriate reagents. (Note: Mer IC50: ++++ means <10 nM; +++ means between 10-100 nM; ++ means between 100 nM-1 μM; + means between 1-30 μM; − means inactive.)

| Structure | Compound_ID | Mer IC$_{50}$ | Physical Data MS m/z (M + 1) or/and $^1$H NMR (400 MHz, CD$_3$OD) |
|---|---|---|---|
| 2 | UNC2433A | ++++ | $^1$H NMR (400 MHz, CD$_3$OD) δ 8.80 (s, 1H), 8.31 (s, 1H), 7.74 (d, J = 8 Hz, 2H), 8.02 (d, J = 4 Hz, 2H), 7.86 (d, J = 4 Hz, 2H), 4.38 (s, 2 H), 3.78-3.72 (m, 1H), 3.71-3.68 (m, 2H), 3.63-3.59 (m, 2H), 3.08 (t, J = 8 Hz, 2H), 2.95-2.87 (m, 1H), 2.20-2.05 (m, 4H), 1.74-1.69 (m, 7H), 1.52-1.50 (m, 5H), 1.04 (t, J = 8 Hz, 3H); MS m/z 512.0 [M + 1]$^+$. |

Example 5

Macrocyclic derivative of 5-(4-((4-methylpiperazin-1-yl)methyl)phenyl)-7H-pyrrolo[2,3-d]pyrimidin-2-amine General Procedure E:

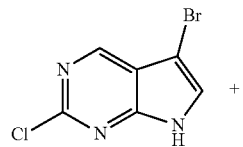

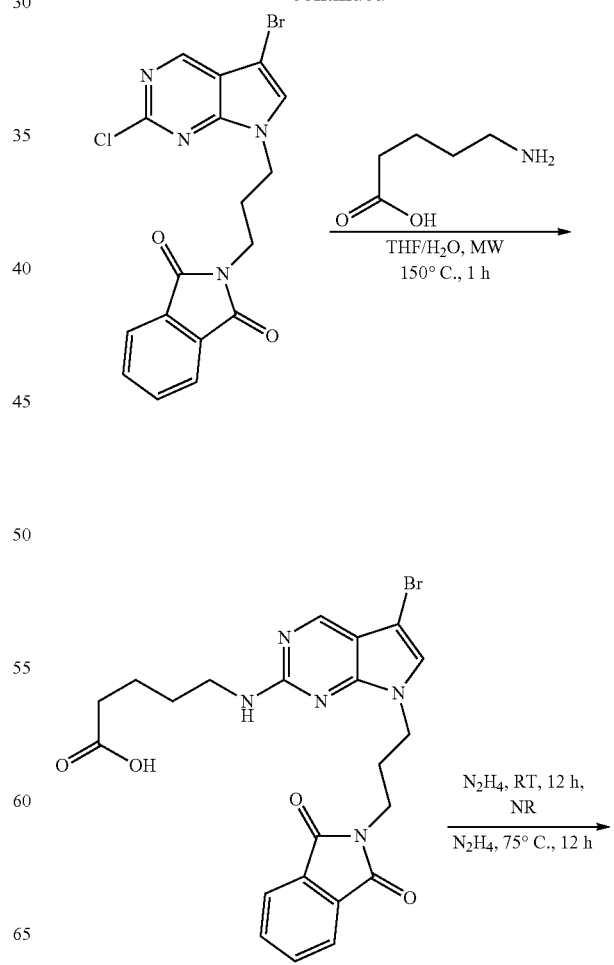

-continued

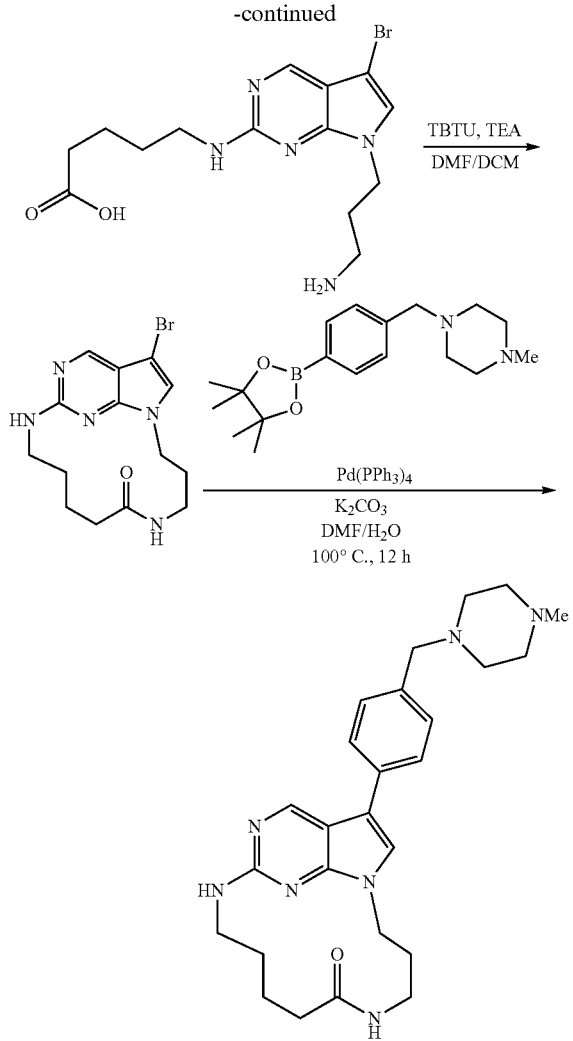

Macrocyclic derivative of 5-(4-((4-methylpiperazin-1-yl)methyl)phenyl)-7H-pyrrolo [2,3-d]pyrimidin-2-amine A suspension of 5-bromo-2-chloro-7H-pyrrolo[2,3-d]pyrimidine (100mg, 0.43 mmol), 2-(3-bromopropyl)isoindoline-1,3-dione (173 mg, 0.65 mmol) and K$_2$CO$_3$ (119 mg, 0.86 mmol) in a mixture of DMSO and THF (8.0 mL, 1:3, v/v) was heated at 100° C. under microwave irradiation for 30 min. The mixture was diluted with ethyl acetate (35 mL), washed with water (3x) and concentrated to provide the crude 2-(3-(5-bromo-2-chloro-7H-pyrrolo[2,3-d]pyrimidin-7-yl)propyl)isoindoline-1,3-dione (MS m/z 420.05 [M+H]$^+$) which was used in next step without further purification.

A solution of the crude 2-(3-(5-bromo-2-chloro-7H-pyrrolo[2,3-d]pyrimidin-7-yl)propyl)isoindoline-1,3-dione in a mixture of THF and water (10 mL, 3:2, v/v) was added 5-aminopentanoic acid (172.3 mg, 1.47 mmol). The resulting mixture was heated at 150° C. under microwave irradiation for 1 h. After the solvent was removed, the residue was dissolved in a mixture of ethanol and water (20 mL, 3:2, v/v) followed by the addition of hydrazine (1.5 mL). Then the reaction mixture was heat at 80° C. for overnight. The solvent was removed and the residue was purified on HPLC to provide 5-((7-(3-aminopropyl)-5-bromo-7H-pyrrolo[2,3-d]pyrimidin-2-yl)amino)pentatonic acid as an clear oil (MS m/z 371.10 [M+]$^+$).

A solution of this clear oil in DMF/DCM (120 mL, 2:3, v/v) was added TBTU (115 mg) and triethylamine (2.2 mL). The reaction mixture was stirred at room temperature for overnight. Solvent was removed and the residue (MS m/z 353.10 [M+H]$^+$) was dissolved in dioxane (6.0 mL) followed by the addition of 4-(4-methylpiperazino)methylphenylboronic acid pinacol ester (135 mg, 0.43 mmol), Pd(PPh$_3$)$_4$ (12 mg, 0.01 mmol), K$_2$CO$_3$ (128 mg, 0.93 mmol) and water (2.0 mL). The resulting mixture was heated at 150° C. under microwave irradiation for 15 min, quenched with water (15 mL), extracted with ethylacetate (4x), dried (MgSO$_4$) and concentrated. The residue was purified on HPLC to give the desired product as a TFA salt. This salt was neutralized with a 7 N NH$_3$ solution in methanol and was purified on ISCO to provide the desired product (UNC2434A) as a white solid. $^1$H NMR (400 MHz, CD$_3$OD) δ 8.66 (s, 1H), 7.60-7.53 (m, 2H), 7.35 (d, J=8.2 Hz, 2H), 7.31 (s, 1H), 5.47 (s, 2H), 4.27 (t, J=7.2 Hz, 2H), 3.54 (s, 2H), 3.47-3.40 (m, 2H), 3.19-3.13 (m, 2H), 2.57-2.46 (m, 6H), 2.42-2.38 (m, 2H), 2.27 (s, 3H), 1.96-1.89 (m, 2H), 1.80-1.71 (m, 2H), 1.71-1.61 (m, 2H); MS m/z 462.30 [M+H]$^+$.

The foregoing is illustrative of the present invention, and is not to be construed as limiting thereof The invention is defined by the following claims, with equivalents of the claims to be included therein.

That which is claimed is:

1. A pharmaceutical composition comprising an effective amount of a compound of Formula I having the following structure:

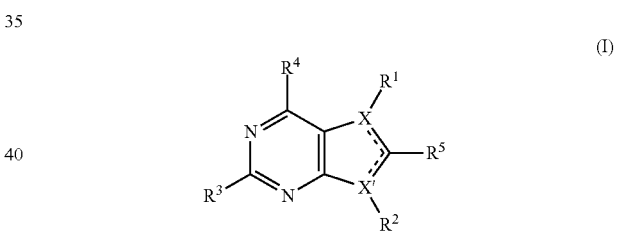

(I)

wherein:
one of X and X' is N and the other of X and X' is C;
one of the dashed lines in Formula I is a single bond and the other of the dashed lines in Formula I is a double bond;
R$^1$ is aryl; wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)m, cycloalkylalkyl-S(O)$_m$, aryl-S(O)$_m$, arylalkyl- S(O)$_m$, heterocyclo-S(O)$_m$, heterocycloalkyl-S(O)m, amino, carboxy, alkylamino, alkenylamino, alkynylamino, haloalkylamino , cycloalkylamino, cycloalkylalkylamino, aryl amino, arylalkylamino, heterocycloamino , heterocycloalkylamino, disubstituted-amino, acylamino, acyloxy, ester, amide, sulfonamide, urea, alkoxyacylamino, aminoacyloxy, nitro or cyano, where m=0, 1 , 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or $R^1$ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl;

$R^2$ is —$R^5R^6$, where $R^5$ is a covalent bond or C1 to C3 alkyl and $R^6$ is cycloalkyl, and wherein $R^6$ is optionally substituted from one to two times with independently selected polar groups;

$R^3$ is —$NR^7R^8$, where $R^7$ and $R^8$ are each independently selected from H, alkyl, arylalkyl; cycloalkylalkyl, heterocycloalkylalkyl, heteroaryalkyl, and alkoxyalkyl, each of which is optionally substituted one, two or three times with independently selected polar groups;

or $R^2$ and $R^3$ together form a linking group;

$R^4$ is H, loweralkyl, halo, or loweralkoxy; and $R^5$ is H, loweralkyl, halo, or loweralkoxy;

or a pharmaceutically acceptable salt thereof; and a pharmaceutically acceptable vehicle.

2. The pharmaceutical composition of claim 1, wherein the compound of Formula I has the following structure:

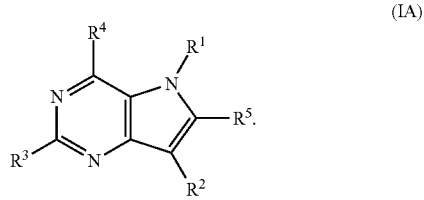

(IA)

3. The pharmaceutical composition of claim 1, wherein the compound of Formula I has the following structure:

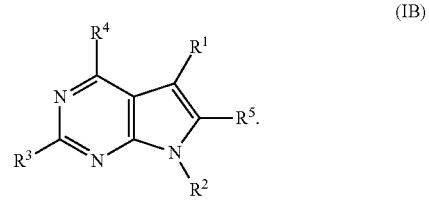

(IB)

4. The pharmaceutical composition of claim 1, wherein $R^1$ is phenyl, or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

5. The pharmaceutical composition of claim 1, wherein $R^1$ is phenyl, wherein the phenyl is substituted from 1 to 3 times with one or a combination of halo or heterocycloalkyl-S(O)$_2$, wherein the heterocycloalkyl-S(O)$_2$ can be substituted from 1 to 3 times with one or a combination of halo, alkyl, or haloalkyl.

6. The pharmaceutical composition of claim 1, wherein $R^1$ is phenyl, wherein the phenyl is substituted once with halo, alkyl, cycloalkyl, heterocycloalkyl, sulfonamide, or heterocycloalkyl-S(O)$_2$, and wherein the alkyl or heterocycloalkyl-S(O)$_2$ can be substituted once with halo, alkyl, haloalkyl, or unsubstituted or substituted heterocycloalkyl, wherein the substituted heterocycloalkyl can be substituted once with alkyl.

7. The pharmaceutical composition of claim 3, wherein $R^1$ is phenyl, wherein the phenyl is substituted from 1 to 3 times with one or a combination of halo or heterocycloalkyl-S(O)$_2$, wherein the heterocycloalkyl-S(O)$_2$ can be substituted from 1 to 3 times with one or a combination of halo, alkyl, or haloalkyl.

8. The pharmaceutical composition of claim 3, wherein $R^1$ is phenyl, wherein the phenyl is substituted once with halo, alkyl, cycloalkyl, heterocycloalkyl, sulfonamide, or heterocycloalkyl-S(O)$_2$, and wherein the alkyl or heterocycloalkyl-S(O)$_2$ can be substituted once with halo, alkyl, haloalkyl, or unsubstituted or substituted heterocycloalkyl, wherein the substituted heterocycloalkyl can be substituted once with alkyl.

9. The pharmaceutical composition of claim 1, wherein the cycloalkyl of $R^6$ is substituted once with amino or hydroxyl.

10. The pharmaceutical composition of claim 9, wherein the cycloalkyl is substituted once with hydroxyl.

11. The pharmaceutical composition of claim 1, wherein $R^5$ is a covalent bond.

12. The pharmaceutical composition of claim 11, wherein $R^7$ is H.

13. The pharmaceutical composition of claim 1, wherein $R^8$ is cycloalkylalkyl.

14. The pharmaceutical composition of claim 1, wherein the compound has the structure:

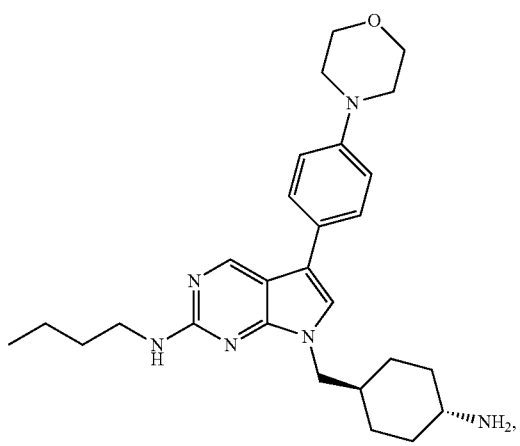
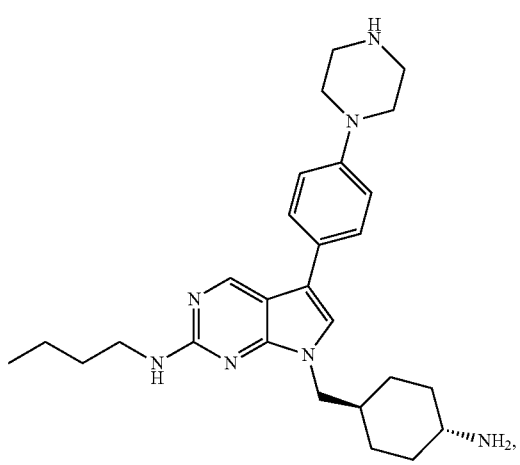
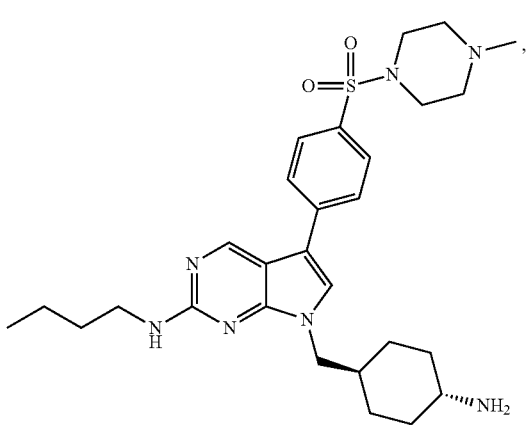
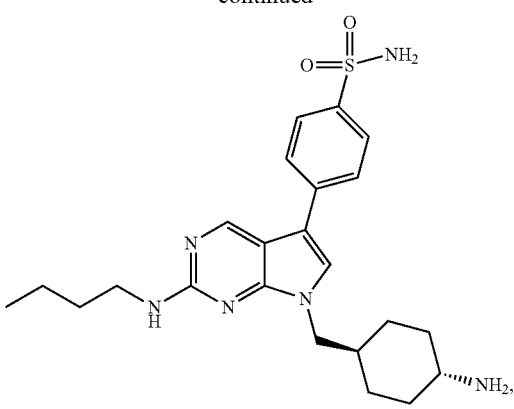
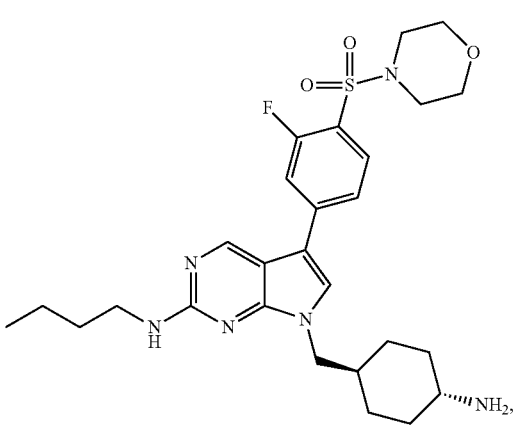
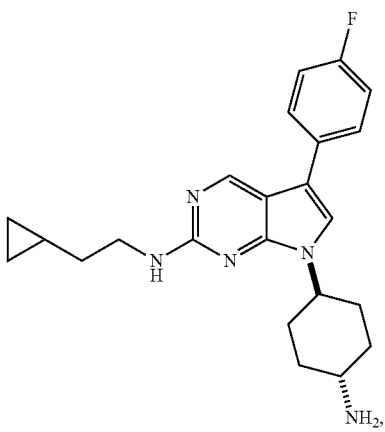

65
-continued
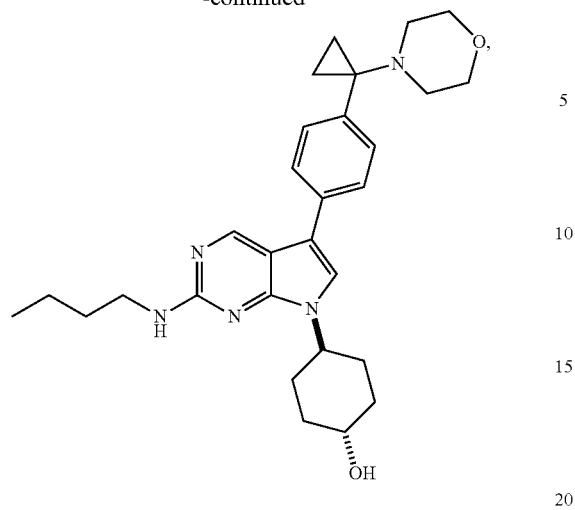
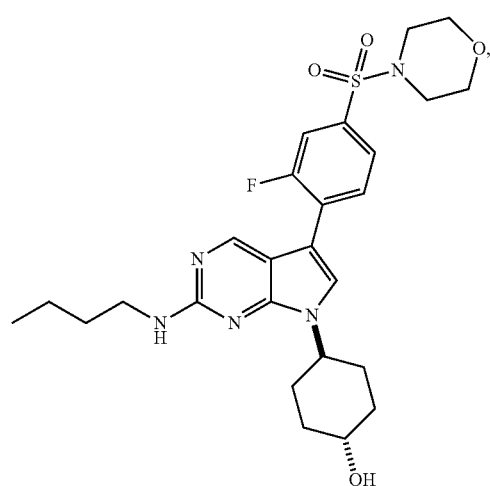
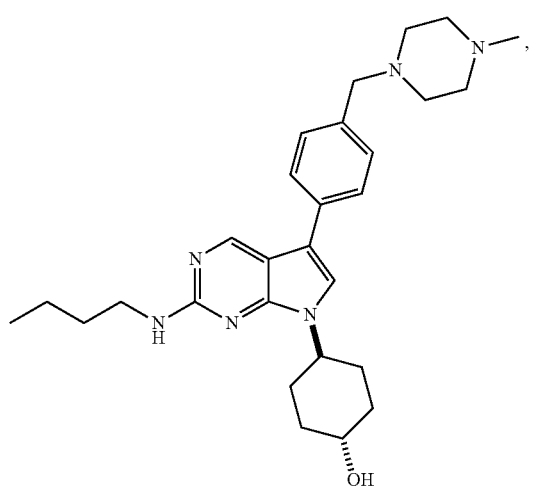
66
-continued
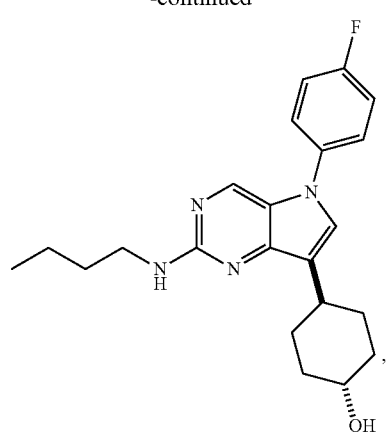
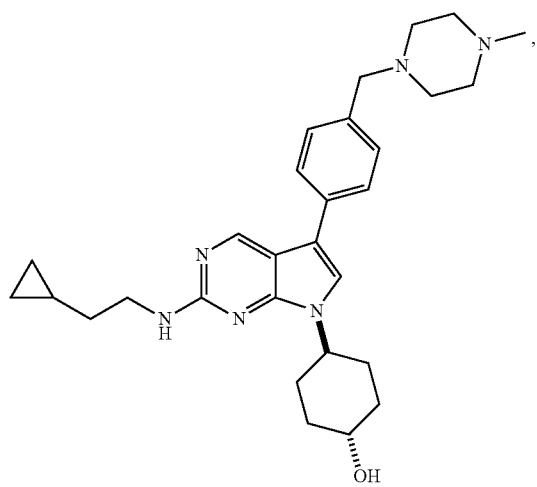
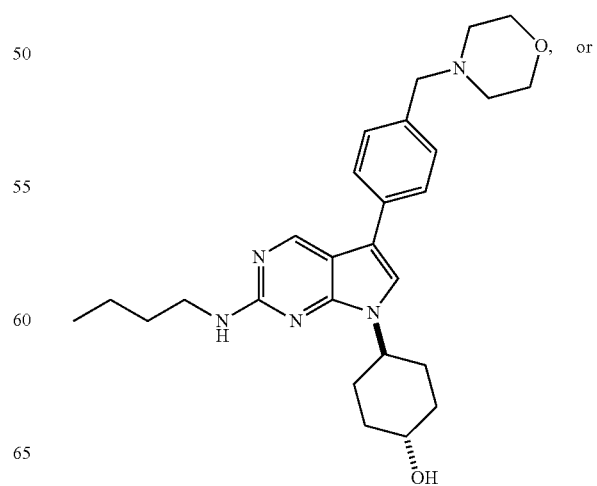

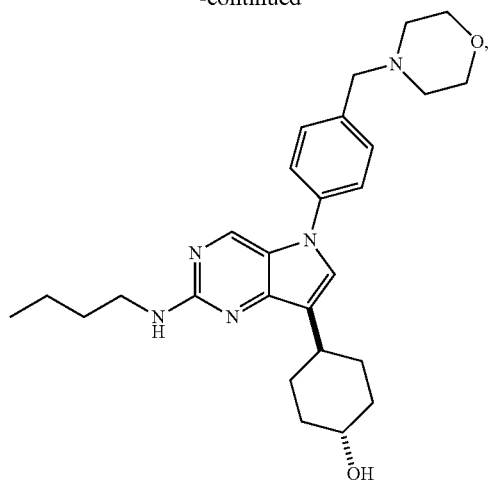

or a pharmaceutically acceptable salt thereof.

15. The pharmaceutical composition of claim 14, wherein the compound has the structure:

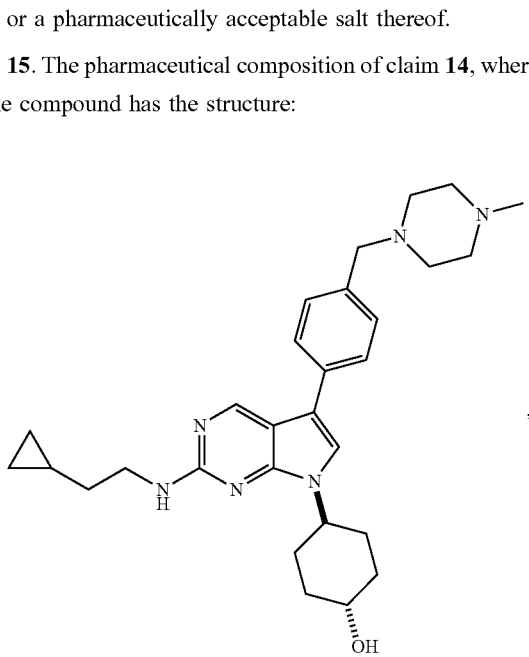

or a pharmaceutically acceptable salt thereof.

16. The pharmaceutical composition of claim 14, wherein the compound has the structure:

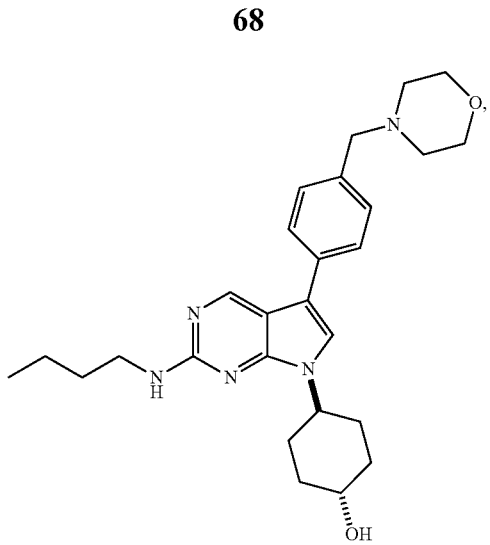

or a pharmaceutically acceptable salt thereof.

17. The pharmaceutical composition of claim 14, wherein the compound has the structure:

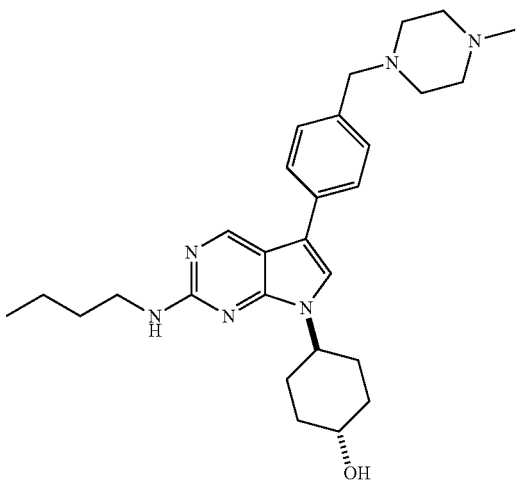

or a pharmaceutically acceptable salt thereof.

18. A method of treating a cancer comprising administering to a subject in need thereof an effective amount of the pharmaceutical composition according to claim 1, wherein the treatment of the cancer is mediated by the inhibition of Mer receptor tyrosine kinase activity.

19. The method of claim 18, wherein the cancer is selected from the group consisting of myeloid leukemia, lymphoblastic leukemia, melanoma, breast, lung, colon, liver, gastric, kidney, ovarian, uterine, and brain cancer.

* * * * *